(12) United States Patent
Pintor et al.

(10) Patent No.: US 9,561,100 B2
(45) Date of Patent: *Feb. 7, 2017

(54) SYSTEMS FOR QUICKLY DELIVERING A PROSTHETIC HEART VALVE

(71) Applicant: Edwards Lifesciences Corporation, Irvine, CA (US)

(72) Inventors: Rafael Pintor, Mission Viejo, CA (US); Mark Chau, Aliso Viejo, CA (US); Travis Oba, Brea, CA (US); August R. Yambao, Temecula, CA (US); Louis A. Campbell, Santa Ana, CA (US); Tammy Huntley, Santa Ana, CA (US); Qinggang Zeng, Aliso Viejo, CA (US); Carey L. Cristea, Lake Forest, CA (US); Faisal Kalam, Corona, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/684,267

(22) Filed: Apr. 10, 2015

(65) Prior Publication Data

US 2015/0216656 A1 Aug. 6, 2015

Related U.S. Application Data

(60) Division of application No. 13/660,780, filed on Oct. 25, 2012, now Pat. No. 9,005,278, which is a
(Continued)

(51) Int. Cl.
A61F 2/24 (2006.01)

(52) U.S. Cl.
CPC ............. *A61F 2/2418* (2013.01); *A61F 2/243* (2013.01); *A61F 2/2409* (2013.01);
(Continued)

(58) Field of Classification Search
CPC ........ A61F 2/24; A61F 2/2409; A61F 2/2433; A61F 2/2412; A61F 2/2427
See application file for complete search history.

(56) References Cited

U.S. PATENT DOCUMENTS

| 3,143,742 A | 8/1964 | Cromie |
| 3,320,972 A | 5/1967 | High et al. |

(Continued)

FOREIGN PATENT DOCUMENTS

| EP | 0125393 A1 | 11/1984 |
| EP | 0143246 A2 | 6/1985 |

(Continued)

*Primary Examiner* — Bruce E Snow
(74) *Attorney, Agent, or Firm* — Guy Cumberbatch; Pui Tong Ho

(57) ABSTRACT

A heart valve prosthesis that can be quickly and easily implanted during a surgical procedure is provided. The prosthetic valve has a base stent that is deployed at a treatment site, and a valve component configured to quickly connect to the base stent. The base stent may take the form of a self- or balloon-expandable stent that expands outward against the native valve with or without leaflet excision. The valve component has a non-expandable prosthetic valve and a self- or balloon-expandable coupling stent for attachment to the base stent, thereby fixing the position of the valve component relative to the base stent. The prosthetic valve may be a commercially available to valve with a sewing ring and the coupling stent attaches to the sewing ring. The system is particularly suited for rapid deployment of heart valves in a conventional open-heart surgical environment. A catheter-based system and method for deployment is provided.

13 Claims, 15 Drawing Sheets

Related U.S. Application Data continuation of application No. 12/635,471, filed on Dec. 10, 2009, now Pat. No. 8,308,798.

(60) Provisional application No. 61/139,398, filed on Dec. 19, 2008.

(52) U.S. Cl.
CPC ...... *A61F 2/2433* (2013.01); *A61F 2220/005* (2013.01); *A61F 2220/0016* (2013.01); *A61F 2220/0025* (2013.01); *A61F 2220/0075* (2013.01); *A61F 2220/0083* (2013.01); *A61F 2230/0054* (2013.01); *A61F 2230/0067* (2013.01); *A61F 2230/0069* (2013.01); *A61F 2230/0078* (2013.01); *A61F 2250/006* (2013.01)

(56) References Cited

U.S. PATENT DOCUMENTS

| | | |
|---|---|---|
| 3,371,352 A | 3/1968 | Siposs et al. |
| 3,409,013 A | 11/1968 | Berry |
| 3,546,710 A | 12/1970 | Shumakov et al. |
| 3,574,865 A | 4/1971 | Hamaker |
| 3,628,535 A | 12/1971 | Ostrowsky et al. |
| 3,755,823 A | 9/1973 | Hancock |
| 3,839,741 A | 10/1974 | Haller |
| 3,997,923 A | 12/1976 | Possis |
| 4,035,849 A | 7/1977 | Angell et al. |
| 4,078,468 A | 3/1978 | Civitello |
| 4,079,468 A | 3/1978 | Liotta et al. |
| 4,084,268 A | 4/1978 | Ionescu et al. |
| 4,106,129 A | 8/1978 | Carpentier et al. |
| 4,172,295 A | 10/1979 | Batten |
| 4,217,665 A | 8/1980 | Bex et al. |
| 4,218,782 A | 8/1980 | Rygg |
| 4,259,753 A | 4/1981 | Liotta et al. |
| RE30,912 E | 4/1982 | Hancock |
| 4,343,048 A | 8/1982 | Ross et al. |
| 4,364,126 A | 12/1982 | Rosen et al. |
| 4,388,735 A | 6/1983 | Ionescu et al. |
| 4,441,216 A | 4/1984 | Ionescu et al. |
| 4,451,936 A | 6/1984 | Carpentier et al. |
| 4,470,157 A | 9/1984 | Love |
| 4,490,859 A | 1/1985 | Black et al. |
| 4,501,030 A | 2/1985 | Lane |
| 4,506,394 A | 3/1985 | Bedard |
| 4,535,483 A | 8/1985 | Klawitter et al. |
| 4,605,407 A | 8/1986 | Black et al. |
| 4,626,255 A | 12/1986 | Reichart et al. |
| 4,629,459 A | 12/1986 | Ionescu et al. |
| 4,680,031 A | 7/1987 | Alonso |
| 4,687,483 A | 8/1987 | Fisher et al. |
| 4,702,250 A | 10/1987 | Ovil et al. |
| 4,705,516 A | 11/1987 | Barone et al. |
| 4,725,274 A | 2/1988 | Lane et al. |
| 4,731,074 A | 3/1988 | Rousseau et al. |
| 4,778,461 A | 10/1988 | Pietsch et al. |
| 4,790,843 A | 12/1988 | Carpentier et al. |
| 4,851,000 A | 7/1989 | Gupta |
| 4,865,600 A | 9/1989 | Carpentier et al. |
| 4,888,009 A | 12/1989 | Lederman et al. |
| 4,914,097 A | 4/1990 | Oda et al. |
| 4,960,424 A | 10/1990 | Grooters |
| 4,993,428 A | 2/1991 | Arms |
| 5,010,892 A | 4/1991 | Colvin et al. |
| 5,032,128 A | 7/1991 | Alonso |
| 5,037,434 A | 8/1991 | Lane |
| 5,147,391 A | 9/1992 | Lane |
| 5,163,955 A | 11/1992 | Love et al. |
| 5,258,023 A | 11/1993 | Reger |
| 5,316,016 A | 5/1994 | Adams et al. |
| 5,326,370 A | 7/1994 | Love et al. |
| 5,326,371 A | 7/1994 | Love et al. |
| 5,332,402 A | 7/1994 | Teitelbaum |
| 5,376,112 A | 12/1994 | Duran |
| 5,396,887 A | 3/1995 | Imran |
| 5,397,351 A | 3/1995 | Pavcnik et al. |
| 5,423,887 A | 6/1995 | Love et al. |
| 5,425,741 A | 6/1995 | Lemp et al. |
| 5,431,676 A | 7/1995 | Dubrul et al. |
| 5,449,384 A | 9/1995 | Johnson |
| 5,449,385 A | 9/1995 | Religa et al. |
| 5,469,868 A | 11/1995 | Reger |
| 5,476,510 A | 12/1995 | Eberhardt et al. |
| 5,488,789 A | 2/1996 | Religa et al. |
| 5,489,297 A | 2/1996 | Duran |
| 5,489,298 A | 2/1996 | Love et al. |
| 5,500,016 A | 3/1996 | Fisher |
| 5,533,515 A | 7/1996 | Coller et al. |
| 5,549,665 A | 8/1996 | Vesely et al. |
| 5,562,729 A | 10/1996 | Purdy et al. |
| 5,571,215 A | 11/1996 | Sterman et al. |
| 5,573,007 A | 11/1996 | Bobo, Sr. |
| 5,578,076 A | 11/1996 | Krueger et al. |
| 5,584,803 A | 12/1996 | Stevens et al. |
| 5,606,928 A | 3/1997 | Religa et al. |
| 5,618,307 A | 4/1997 | Donlon et al. |
| 5,626,607 A | 5/1997 | Malecki et al. |
| 5,628,789 A | 5/1997 | Vanney et al. |
| 5,662,705 A | 9/1997 | Love et al. |
| 5,693,090 A | 12/1997 | Unsworth et al. |
| 5,695,503 A | 12/1997 | Krueger et al. |
| 5,713,952 A | 2/1998 | Vanney et al. |
| 5,716,370 A | 2/1998 | Williamson, IV et al. |
| 5,728,064 A | 3/1998 | Burns et al. |
| 5,728,151 A | 3/1998 | Garrison et al. |
| 5,735,894 A | 4/1998 | Krueger et al. |
| 5,752,522 A | 5/1998 | Murphy |
| 5,755,782 A | 5/1998 | Love et al. |
| 5,766,240 A | 6/1998 | Johnson |
| 5,776,187 A | 7/1998 | Krueger et al. |
| 5,800,527 A | 9/1998 | Jansen et al. |
| 5,814,097 A | 9/1998 | Sterman et al. |
| 5,814,098 A | 9/1998 | Hinnenkamp et al. |
| 5,824,064 A | 10/1998 | Taheri |
| 5,824,068 A | 10/1998 | Bugge |
| 5,840,081 A | 11/1998 | Andersen et al. |
| 5,848,969 A | 12/1998 | Panescu et al. |
| 5,855,563 A | 1/1999 | Kaplan et al. |
| 5,855,601 A | 1/1999 | Bessler et al. |
| 5,865,801 A | 2/1999 | Houser |
| 5,891,160 A | 4/1999 | Williamson, IV et al. |
| 5,895,420 A | 4/1999 | Mirsch, II et al. |
| 5,902,308 A | 5/1999 | Murphy |
| 5,904,695 A | 5/1999 | Krueger |
| 5,908,450 A | 6/1999 | Gross et al. |
| 5,919,147 A | 7/1999 | Jain |
| 5,921,934 A | 7/1999 | Teo |
| 5,921,935 A | 7/1999 | Hickey |
| 5,924,984 A | 7/1999 | Rao |
| 5,957,949 A | 9/1999 | Leonhardt et al. |
| 5,972,004 A | 10/1999 | Williamson, IV et al. |
| 5,984,959 A | 11/1999 | Robertson et al. |
| 5,984,973 A | 11/1999 | Girard et al. |
| 6,010,531 A | 1/2000 | Donlon et al. |
| 6,042,607 A | 3/2000 | Williamson, IV et al. |
| 6,066,160 A | 5/2000 | Colvin et al. |
| 6,074,418 A | 6/2000 | Buchanan et al. |
| 6,081,737 A | 6/2000 | Shah |
| 6,083,179 A | 7/2000 | Oredsson |
| 6,099,475 A | 8/2000 | Seward et al. |
| 6,106,550 A | 8/2000 | Magovern et al. |
| 6,110,200 A | 8/2000 | Hinnenkamp |
| 6,117,091 A | 9/2000 | Young et al. |
| 6,126,007 A | 10/2000 | Kari et al. |
| 6,162,233 A | 12/2000 | Williamson, IV et al. |
| 6,168,614 B1 | 1/2001 | Andersen et al. |
| 6,176,877 B1 | 1/2001 | Buchanan et al. |
| 6,197,054 B1 | 3/2001 | Hamblin, Jr. et al. |
| 6,217,611 B1 | 4/2001 | Klostermeyer |
| 6,231,561 B1 | 5/2001 | Frazier et al. |
| 6,241,765 B1 | 6/2001 | Griffin et al. |

(56) References Cited

U.S. PATENT DOCUMENTS

| | | |
|---|---|---|
| 6,245,102 B1 | 6/2001 | Jayaraman |
| 6,264,611 B1 | 7/2001 | Ishikawa et al. |
| 6,283,127 B1 | 9/2001 | Sterman et al. |
| 6,287,339 B1 | 9/2001 | Vazquez et al. |
| 6,290,674 B1 | 9/2001 | Roue et al. |
| 6,312,447 B1 | 11/2001 | Grimes |
| 6,312,465 B1 | 11/2001 | Griffin et al. |
| 6,322,526 B1 | 11/2001 | Rosenman et al. |
| 6,328,727 B1 | 12/2001 | Frazier et al. |
| 6,350,282 B1 | 2/2002 | Eberhardt |
| 6,371,983 B1 | 4/2002 | Lane |
| 6,375,620 B1 | 4/2002 | Oser et al. |
| 6,402,780 B2 | 6/2002 | Williamson, IV et al. |
| 6,425,916 B1 | 7/2002 | Garrison et al. |
| 6,440,164 B1 | 8/2002 | DiMatteo et al. |
| 6,454,799 B1 | 9/2002 | Schreck |
| 6,458,153 B1 | 10/2002 | Bailey et al. |
| 6,468,305 B1 | 10/2002 | Otte |
| 6,491,624 B1 | 12/2002 | Lotfi |
| 6,582,462 B1 | 6/2003 | Andersen et al. |
| 6,585,766 B1 | 7/2003 | Huynh et al. |
| 6,651,671 B1 | 11/2003 | Donlon et al. |
| 6,652,578 B2 | 11/2003 | Bailey et al. |
| 6,682,559 B2 | 1/2004 | Myers et al. |
| 6,685,739 B2 | 2/2004 | DiMatteo et al. |
| 6,719,789 B2 | 4/2004 | Cox |
| 6,730,118 B2 | 5/2004 | Spenser et al. |
| 6,733,525 B2 | 5/2004 | Yang et al. |
| 6,764,508 B1 | 7/2004 | Roehe et al. |
| 6,767,362 B2 | 7/2004 | Schreck |
| 6,786,925 B1 | 9/2004 | Schoon et al. |
| 6,790,229 B1 | 9/2004 | Berreklouw |
| 6,790,230 B2 | 9/2004 | Beyersdorf et al. |
| 6,805,711 B2 | 10/2004 | Quijano et al. |
| 6,893,459 B1 | 5/2005 | Macoviak |
| 6,893,460 B2 | 5/2005 | Spenser et al. |
| 6,908,481 B2 | 6/2005 | Cribier |
| 6,939,365 B1 | 9/2005 | Fogarty et al. |
| 7,011,681 B2 | 3/2006 | Vesely |
| 7,025,780 B2 | 4/2006 | Gabbay |
| 7,070,616 B2 | 7/2006 | Majercak et al. |
| 7,097,659 B2 | 8/2006 | Woolfson et al. |
| 7,101,396 B2 | 9/2006 | Artof et al. |
| 7,147,663 B1 | 12/2006 | Berg et al. |
| 7,153,324 B2 | 12/2006 | Case et al. |
| 7,195,641 B2 | 3/2007 | Palmaz et al. |
| 7,201,771 B2 | 4/2007 | Lane |
| 7,201,772 B2 | 4/2007 | Schwammenthal et al. |
| 7,238,200 B2 | 7/2007 | Lee et al. |
| 7,252,682 B2 | 8/2007 | Seguin |
| 7,261,732 B2 | 8/2007 | Justino |
| RE40,377 E | 6/2008 | Williamson, IV et al. |
| 7,422,603 B2 | 9/2008 | Lane |
| 7,513,909 B2 | 4/2009 | Lane et al. |
| 7,556,647 B2 | 7/2009 | Drews et al. |
| 7,569,072 B2 | 8/2009 | Berg et al. |
| 8,308,798 B2 | 11/2012 | Pintor et al. |
| 8,348,998 B2 | 1/2013 | Pintor et al. |
| 8,734,505 B2 | 5/2014 | Goldfarb et al. |
| 9,005,278 B2 | 4/2015 | Pintor et al. |
| 2001/0039435 A1 | 11/2001 | Roue et al. |
| 2001/0039436 A1 | 11/2001 | Frazier et al. |
| 2001/0041914 A1 | 11/2001 | Frazier et al. |
| 2001/0041915 A1 | 11/2001 | Roue et al. |
| 2001/0049492 A1 | 12/2001 | Frazier et al. |
| 2002/0015970 A1 | 2/2002 | Murray et al. |
| 2002/0026238 A1 | 2/2002 | Lane et al. |
| 2002/0032481 A1 | 3/2002 | Gabbay |
| 2002/0058995 A1 | 5/2002 | Stevens |
| 2002/0123802 A1 | 9/2002 | Snyders |
| 2002/0138138 A1 | 9/2002 | Yang |
| 2002/0188348 A1 | 12/2002 | DiMatteo et al. |
| 2002/0198594 A1 | 12/2002 | Schreck |
| 2003/0014104 A1 | 1/2003 | Cribier |
| 2003/0023300 A1 | 1/2003 | Bailey et al. |
| 2003/0023303 A1 | 1/2003 | Palmaz et al. |
| 2003/0036795 A1 | 2/2003 | Andersen et al. |
| 2003/0040792 A1 | 2/2003 | Gabbay |
| 2003/0055495 A1 | 3/2003 | Pease et al. |
| 2003/0105519 A1 | 6/2003 | Fasol et al. |
| 2003/0109924 A1 | 6/2003 | Cribier |
| 2003/0114913 A1 | 6/2003 | Spenser et al. |
| 2003/0130729 A1 | 7/2003 | Paniagua et al. |
| 2003/0167089 A1 | 9/2003 | Lane |
| 2003/0236568 A1 | 12/2003 | Hojeibane et al. |
| 2004/0019374 A1 | 1/2004 | Hojeibane et al. |
| 2004/0034411 A1 | 2/2004 | Quijano et al. |
| 2004/0044406 A1 | 3/2004 | Woolfson et al. |
| 2004/0106976 A1 | 6/2004 | Bailey et al. |
| 2004/0122514 A1 | 6/2004 | Fogarty et al. |
| 2004/0122516 A1 | 6/2004 | Fogarty et al. |
| 2004/0167573 A1 | 8/2004 | Williamson et al. |
| 2004/0186563 A1 | 9/2004 | Lobbi |
| 2004/0186565 A1 | 9/2004 | Schreck |
| 2004/0193261 A1 | 9/2004 | Berreklouw |
| 2004/0206363 A1 | 10/2004 | McCarthy et al. |
| 2004/0210304 A1 | 10/2004 | Seguin et al. |
| 2004/0210307 A1 | 10/2004 | Khairkhahan |
| 2004/0225355 A1 | 11/2004 | Stevens |
| 2004/0236411 A1 | 11/2004 | Sarac et al. |
| 2004/0260389 A1 | 12/2004 | Case et al. |
| 2004/0260390 A1 | 12/2004 | Sarac et al. |
| 2005/0010285 A1 | 1/2005 | Lambrecht et al. |
| 2005/0023618 A1 | 2/2005 | Kameda |
| 2005/0027348 A1 | 2/2005 | Case et al. |
| 2005/0033398 A1 | 2/2005 | Seguin |
| 2005/0043760 A1 | 2/2005 | Fogarty et al. |
| 2005/0043790 A1 | 2/2005 | Seguin |
| 2005/0060029 A1 | 3/2005 | Le et al. |
| 2005/0065594 A1 | 3/2005 | DiMatteo et al. |
| 2005/0065614 A1 | 3/2005 | Stinson |
| 2005/0075584 A1 | 4/2005 | Cali |
| 2005/0075713 A1 | 4/2005 | Biancucci et al. |
| 2005/0075717 A1 | 4/2005 | Nguyen et al. |
| 2005/0075718 A1 | 4/2005 | Nguyen et al. |
| 2005/0075719 A1 | 4/2005 | Bergheim |
| 2005/0075720 A1 | 4/2005 | Nguyen et al. |
| 2005/0075724 A1 | 4/2005 | Svanidze et al. |
| 2005/0080454 A1 | 4/2005 | Drews et al. |
| 2005/0096738 A1 | 5/2005 | Cali et al. |
| 2005/0137682 A1 | 6/2005 | Justino |
| 2005/0137686 A1 | 6/2005 | Salahieh et al. |
| 2005/0137687 A1 | 6/2005 | Salahieh et al. |
| 2005/0137688 A1 | 6/2005 | Salahieh et al. |
| 2005/0137690 A1 | 6/2005 | Salahieh et al. |
| 2005/0137692 A1 | 6/2005 | Haug et al. |
| 2005/0137695 A1 | 6/2005 | Salahieh et al. |
| 2005/0159811 A1 | 7/2005 | Lane |
| 2005/0165479 A1 | 7/2005 | Drews et al. |
| 2005/0182486 A1 | 8/2005 | Gabbay |
| 2005/0192665 A1 | 9/2005 | Spenser et al. |
| 2005/0203616 A1 | 9/2005 | Cribier |
| 2005/0203617 A1 | 9/2005 | Forster et al. |
| 2005/0216079 A1 | 9/2005 | MaCoviak |
| 2005/0222674 A1 | 10/2005 | Paine |
| 2005/0234546 A1 | 10/2005 | Nugent et al. |
| 2005/0240263 A1 | 10/2005 | Fogarty et al. |
| 2005/0251252 A1 | 11/2005 | Stobie |
| 2005/0261765 A1 | 11/2005 | Liddicoat |
| 2005/0283231 A1 | 12/2005 | Haug et al. |
| 2006/0025857 A1 | 2/2006 | Bergheim et al. |
| 2006/0052867 A1 | 3/2006 | Revuelta et al. |
| 2006/0058871 A1 | 3/2006 | Zakay et al. |
| 2006/0058872 A1 | 3/2006 | Salahieh et al. |
| 2006/0074484 A1 | 4/2006 | Huber |
| 2006/0085060 A1 | 4/2006 | Campbell |
| 2006/0095125 A1 | 5/2006 | Chinn et al. |
| 2006/0122634 A1 | 6/2006 | Ino et al. |
| 2006/0149360 A1 | 7/2006 | Schwammenthal et al. |
| 2006/0154230 A1 | 7/2006 | Cunanan et al. |
| 2006/0167543 A1 | 7/2006 | Bailey et al. |
| 2006/0195184 A1 | 8/2006 | Lane et al. |
| 2006/0195185 A1 | 8/2006 | Lane et al. |
| 2006/0195186 A1 | 8/2006 | Drews et al. |

(56) References Cited

U.S. PATENT DOCUMENTS

| | | |
|---|---|---|
| 2006/0207031 A1 | 9/2006 | Cunanan et al. |
| 2006/0241745 A1 | 10/2006 | Solem |
| 2006/0246888 A1 | 11/2006 | Bender et al. |
| 2006/0259136 A1 | 11/2006 | Nguyen et al. |
| 2006/0271172 A1 | 11/2006 | Tehrani |
| 2006/0271175 A1 | 11/2006 | Woolfson et al. |
| 2006/0287717 A1 | 12/2006 | Rowe et al. |
| 2006/0287719 A1 | 12/2006 | Rowe et al. |
| 2007/0005129 A1 | 1/2007 | Damm et al. |
| 2007/0010876 A1 | 1/2007 | Salahieh et al. |
| 2007/0016285 A1 | 1/2007 | Lane et al. |
| 2007/0016286 A1 | 1/2007 | Herrmann et al. |
| 2007/0016288 A1 | 1/2007 | Gurskis et al. |
| 2007/0043435 A1 | 2/2007 | Seguin et al. |
| 2007/0078509 A1 | 4/2007 | Lotfy |
| 2007/0078510 A1 | 4/2007 | Ryan |
| 2007/0100440 A1 | 5/2007 | Figulla et al. |
| 2007/0129794 A1 | 6/2007 | Realyvasquez |
| 2007/0142906 A1 | 6/2007 | Figulla et al. |
| 2007/0142907 A1 | 6/2007 | Moaddeb et al. |
| 2007/0150053 A1 | 6/2007 | Gurskis et al. |
| 2007/0156233 A1 | 7/2007 | Kapadia et al. |
| 2007/0162103 A1 | 7/2007 | Case et al. |
| 2007/0162107 A1 | 7/2007 | Haug et al. |
| 2007/0162111 A1 | 7/2007 | Fukamachi et al. |
| 2007/0179604 A1 | 8/2007 | Lane |
| 2007/0185565 A1 | 8/2007 | Schwammenthal et al. |
| 2007/0198097 A1 | 8/2007 | Zegdi |
| 2007/0203575 A1 | 8/2007 | Forster et al. |
| 2007/0203576 A1 | 8/2007 | Lee et al. |
| 2007/0213813 A1 | 9/2007 | Von Segesser et al. |
| 2007/0225801 A1 | 9/2007 | Drews et al. |
| 2007/0233237 A1 | 10/2007 | Krivoruchko |
| 2007/0239266 A1 | 10/2007 | Birdsall |
| 2007/0239269 A1 | 10/2007 | Dolan et al. |
| 2007/0239273 A1 | 10/2007 | Allen |
| 2007/0255398 A1 | 11/2007 | Yang et al. |
| 2007/0260305 A1 | 11/2007 | Drews et al. |
| 2007/0265701 A1 | 11/2007 | Gurskis et al. |
| 2007/0270944 A1 | 11/2007 | Bergheim et al. |
| 2007/0282436 A1* | 12/2007 | Pinchuk ............ A61F 2/2418 623/2.11 |
| 2007/0288089 A1 | 12/2007 | Gurskis et al. |
| 2008/0033543 A1 | 2/2008 | Gurskis et al. |
| 2008/0119875 A1 | 5/2008 | Ino et al. |
| 2008/0319543 A1 | 12/2008 | Lane |
| 2009/0036903 A1 | 2/2009 | Ino et al. |
| 2009/0192599 A1 | 7/2009 | Lane et al. |
| 2009/0192602 A1 | 7/2009 | Kuehn |
| 2009/0192603 A1 | 7/2009 | Ryan |
| 2009/0192604 A1 | 7/2009 | Gloss |
| 2009/0192605 A1 | 7/2009 | Gloss et al. |
| 2009/0192606 A1 | 7/2009 | Gloss et al. |

FOREIGN PATENT DOCUMENTS

| | | |
|---|---|---|
| GB | 2279134 A | 12/1994 |
| SU | 1116573 A1 | 7/1985 |
| WO | 9213502 A1 | 8/1992 |
| WO | 9742871 A1 | 11/1997 |

* cited by examiner

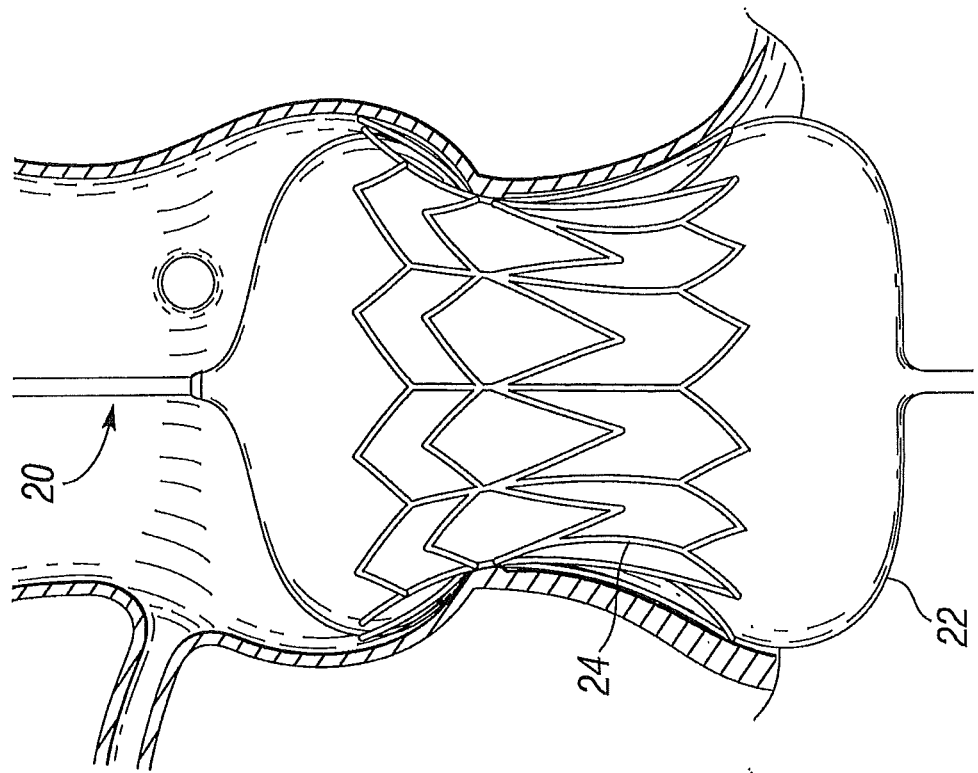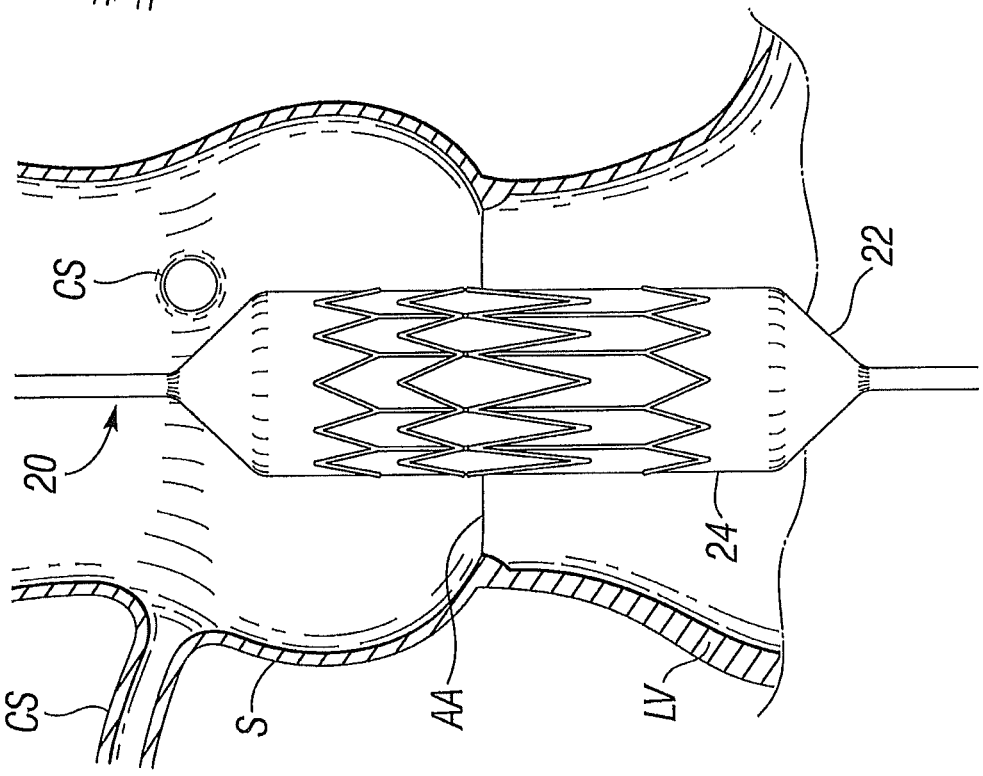

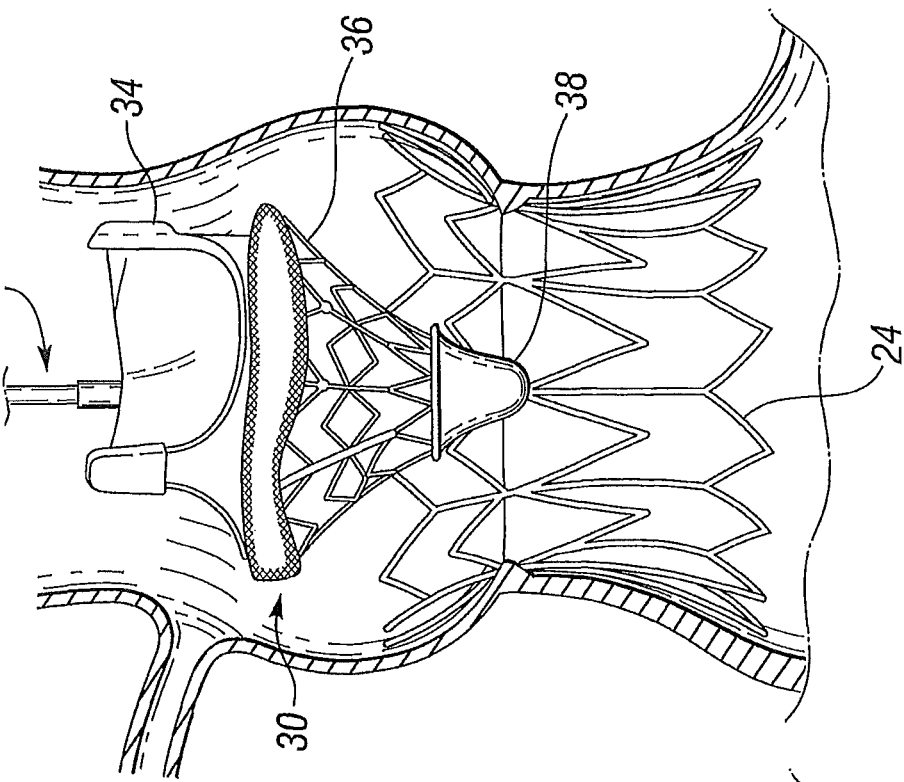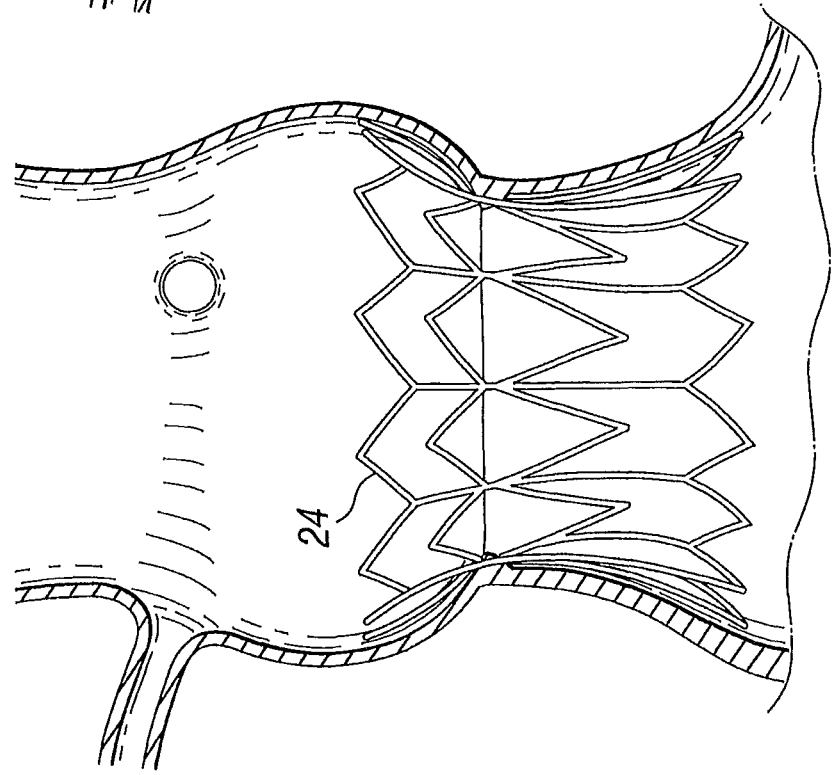

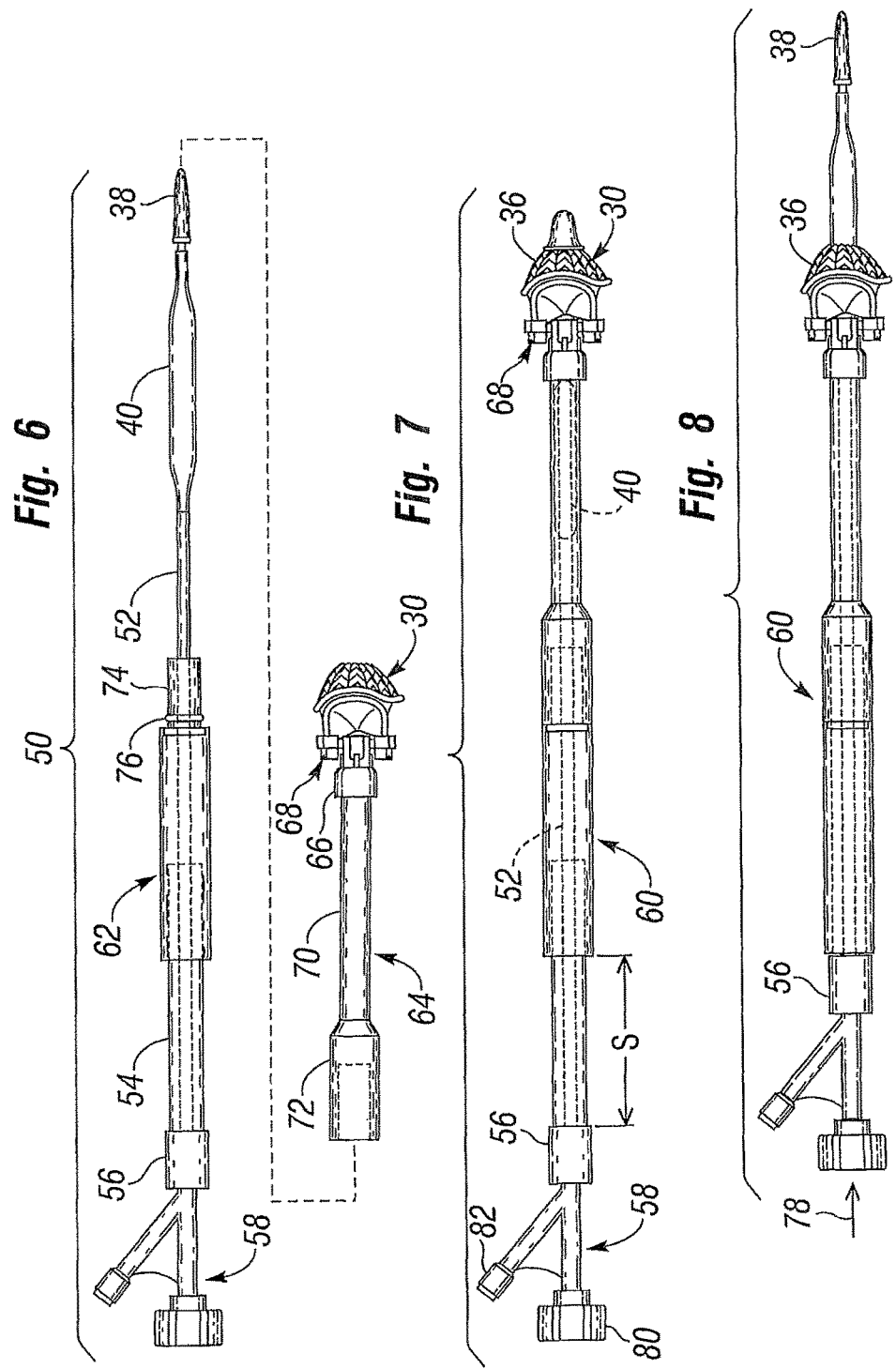

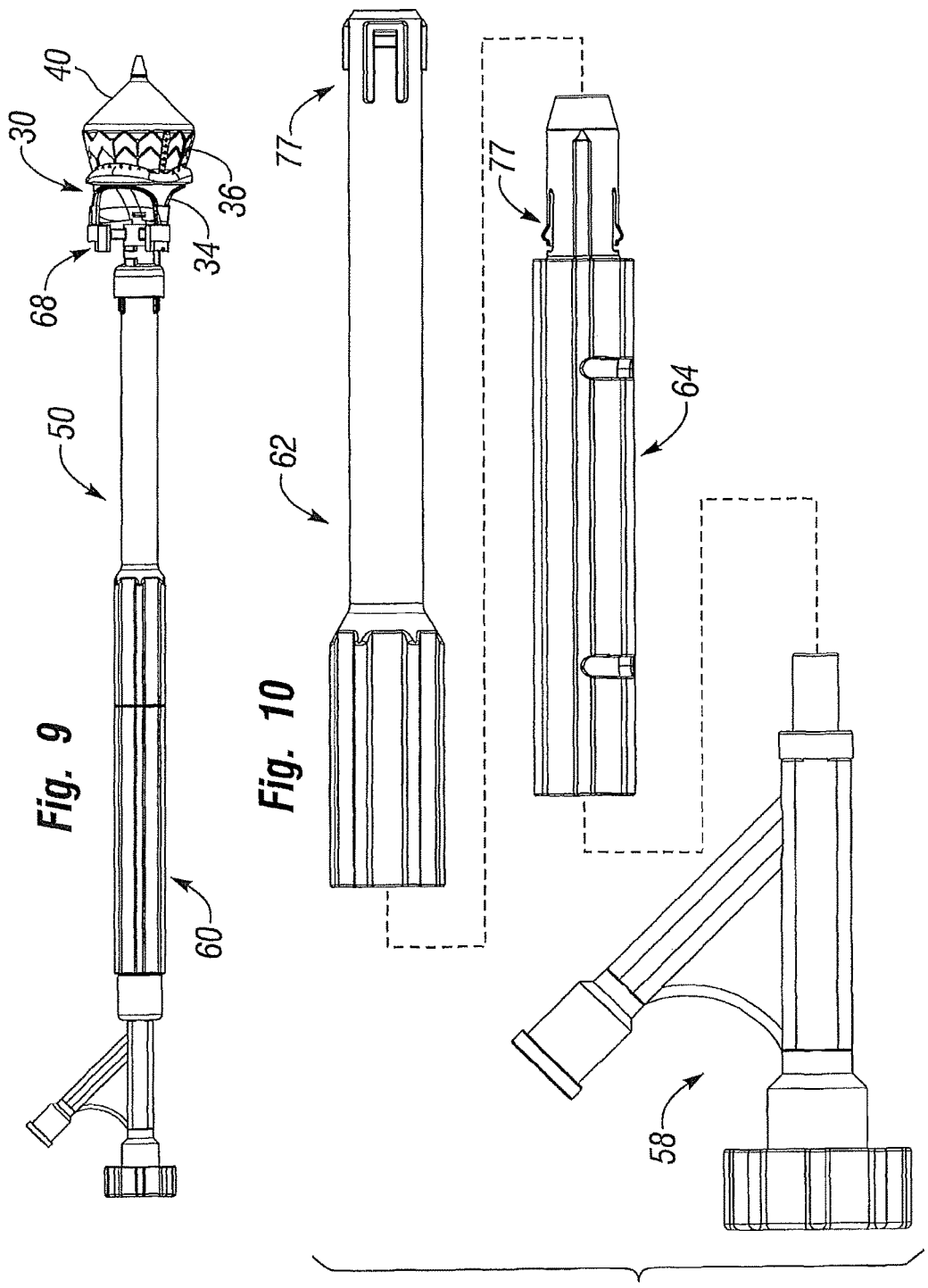

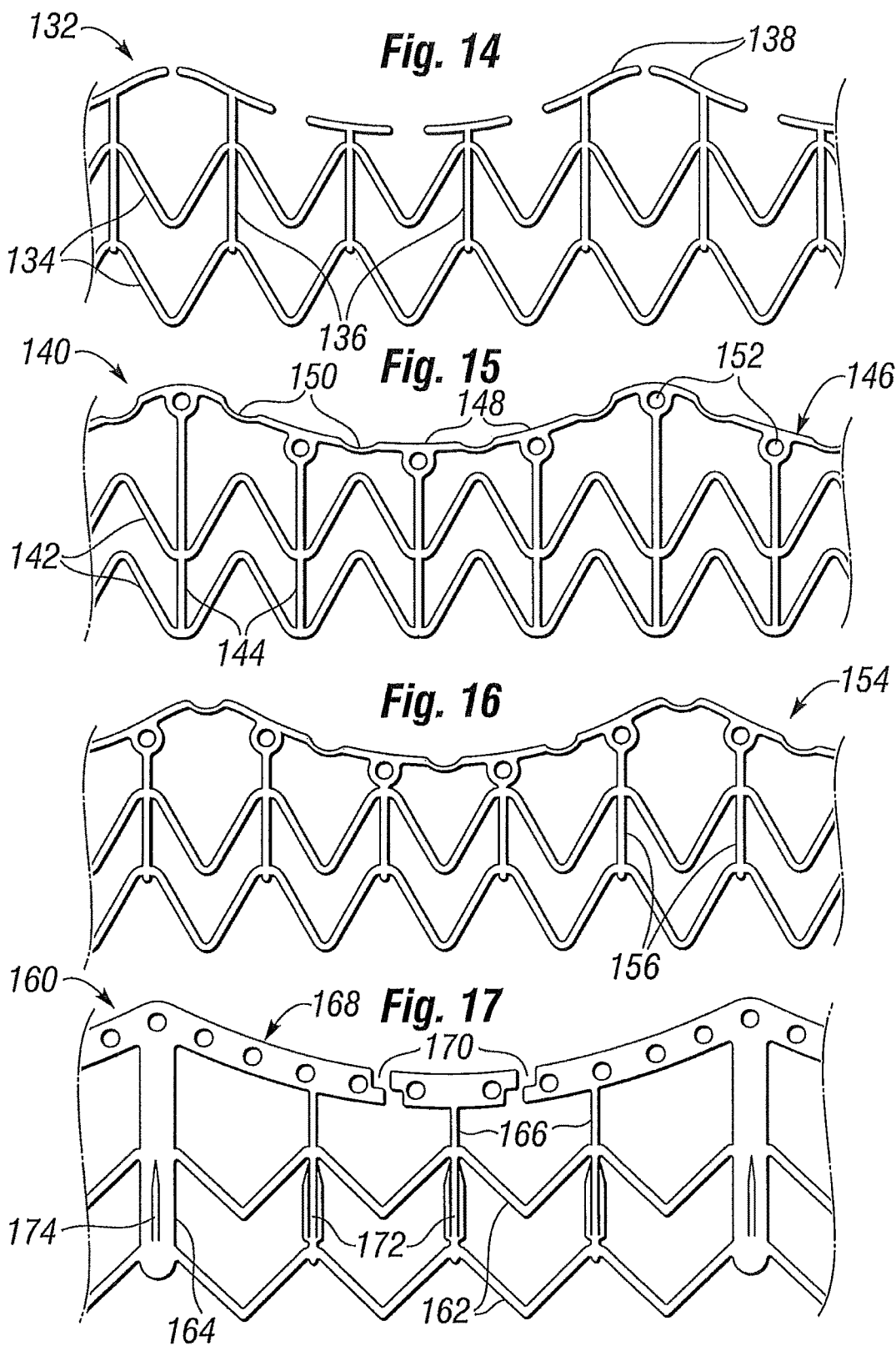

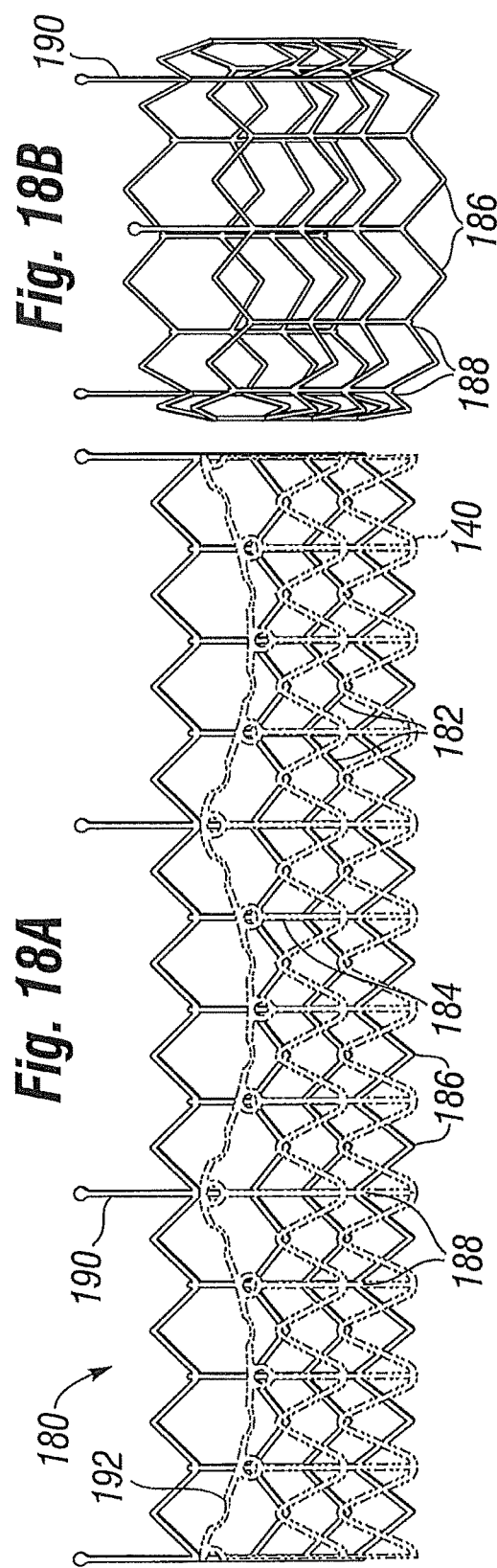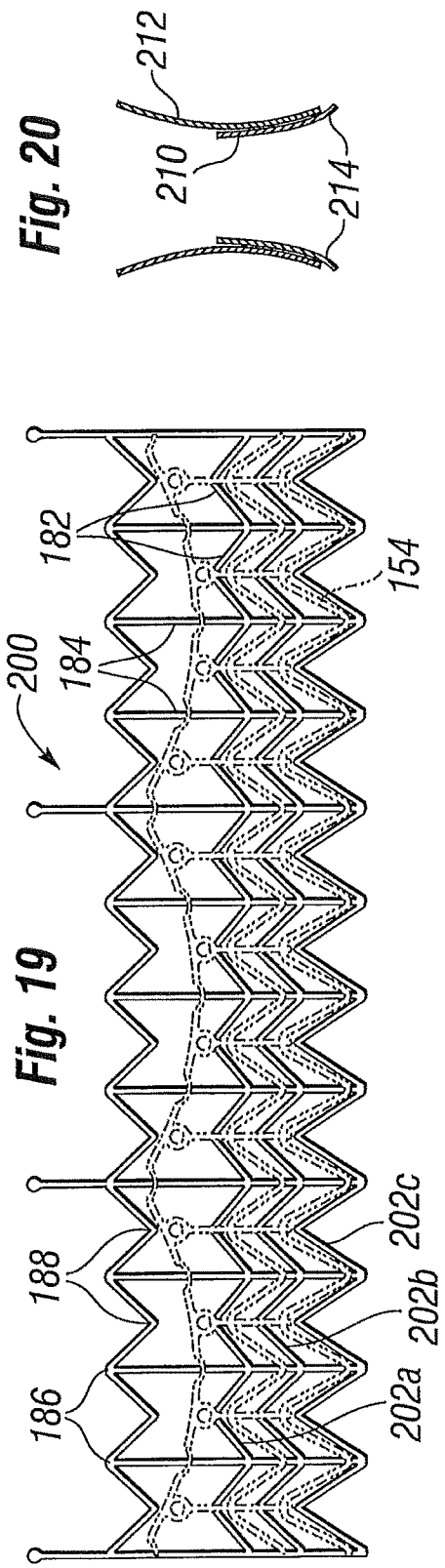

SYSTEMS FOR QUICKLY DELIVERING A PROSTHETIC HEART VALVE

RELATED APPLICATIONS

This application is a divisional of U.S. patent application Ser. No. 13/660,780, filed Oct. 25, 2012, now U.S. Pat. No. 9,005,278, which is a continuation of U.S. patent application Ser. No. 12/635,471, filed Dec. 10, 2009, now U.S. Pat. No. 8,308,798, which claims the benefit of U.S. Patent Application No. 61/139,398, filed Dec. 19, 2008, the entire disclosures of which are incorporated by reference.

FIELD OF THE INVENTION

The present invention generally relates to prosthetic valves for implantation in body channels. More particularly, the present invention relates to prosthetic heart valves configured to be surgically implanted in less time than current valves.

BACKGROUND OF THE INVENTION

In vertebrate animals, the heart is a hollow muscular organ having four pumping chambers as seen in FIG. 1: the left and right atria and the left and right ventricles, each provided with its own one-way valve. The natural heart valves are identified as the aortic, mitral (or bicuspid), tricuspid and pulmonary, and are each mounted in an annulus comprising dense fibrous rings attached either directly or indirectly to the atrial and ventricular muscle fibers. Each annulus defines a flow orifice.

The atria are the blood-receiving chambers, which pump blood into the ventricles. The ventricles are the blood-discharging chambers. A wall composed of fibrous and muscular parts, called the interatrial septum separates the right and left atria (see FIGS. 2 to 4). The fibrous interatrial septum is a materially stronger tissue structure compared to the more friable muscle tissue of the heart. An anatomic landmark on the interatrial septum is an oval, thumbprint sized depression called the oval fossa, or fossa ovalis (shown in FIG. 4).

The synchronous pumping actions of the left and right sides of the heart constitute the cardiac cycle. The cycle begins with a period of ventricular relaxation, called ventricular diastole. The cycle ends with a period of ventricular contraction, called ventricular systole. The four valves (see FIGS. 2 and 3) ensure that blood does not flow in the wrong direction during the cardiac cycle; that is, to ensure that the blood does not back flow from the ventricles into the corresponding atria, or back flow from the arteries into the corresponding ventricles. The mitral valve is between the left atrium and the left ventricle, the tricuspid valve between the right atrium and the right ventricle, the pulmonary valve is at the opening of the pulmonary artery, and the aortic valve is at the opening of the aorta.

FIGS. 2 and 3 show the anterior (A) portion of the mitral valve annulus abutting the non-coronary leaflet of the aortic valve. The mitral valve annulus is in the vicinity of the circumflex branch of the left coronary artery, and the posterior (P) side is near the coronary sinus and its tributaries.

The mitral and tricuspid valves are defined by fibrous rings of collagen, each called an annulus, which forms a part of the fibrous skeleton of the heart. The annulus provides peripheral attachments for the two cusps or leaflets of the mitral valve (called the anterior and posterior cusps) and the three cusps or leaflets of the tricuspid valve. The free edges of the leaflets connect to chordae tendineae from more than one papillary muscle, as seen in FIG. 1. In a healthy heart, these muscles and their tendinous chords support the mitral and tricuspid valves, allowing the leaflets to resist the high pressure developed during contractions (pumping) of the left and right ventricles.

When the left ventricle contracts after filling with blood from the left atrium, the walls of the ventricle move inward and release some of the tension from the papillary muscle and chords. The blood pushed up against the under-surface of the mitral leaflets causes them to rise toward the annulus plane of the mitral valve. As they progress toward the annulus, the leading edges of the anterior and posterior leaflet come together forming a seal and closing the valve. In the healthy heart, leaflet coaptation occurs near the plane of the mitral annulus. The blood continues to be pressurized in the left ventricle until it is ejected into the aorta. Contraction of the papillary muscles is simultaneous with the contraction of the ventricle and serves to keep healthy valve leaflets tightly shut at peak contraction pressures exerted by the ventricle.

Various surgical techniques may be used to repair a diseased or damaged valve. In a valve replacement operation, the damaged leaflets are excised and the annulus sculpted to receive a replacement valve. Due to aortic stenosis and other heart valve diseases, thousands of patients undergo surgery each year wherein the defective native heart valve is replaced by a prosthetic valve, either bioprosthetic or mechanical. Another less drastic method for treating defective valves is through repair or reconstruction, which is typically used on minimally calcified valves. The problem with surgical therapy is the significant insult it imposes on these chronically ill patients with high morbidity and mortality rates associated with surgical repair.

When the valve is replaced, surgical implantation of the prosthetic valve typically requires an open-chest surgery during which the heart is stopped and patient placed on cardiopulmonary bypass (a so-called "heart-lung machine"). In one common surgical procedure, the diseased native valve leaflets are excised and a prosthetic valve is sutured to the surrounding tissue at the valve annulus. Because of the trauma associated with the procedure and the attendant duration of extracorporeal blood circulation, some patients do not survive the surgical procedure or die shortly thereafter. It is well known that the risk to the patient increases with the amount of time required on extracorporeal circulation. Due to these risks, a substantial number of patients with defective valves are deemed inoperable because their condition is too frail to withstand the procedure. By some estimates, about 30 to 50% of the subjects suffering from aortic stenosis who are older than 80 years cannot be operated on for aortic valve replacement.

Because of the drawbacks associated with conventional open-heart surgery, percutaneous and minimally-invasive surgical approaches are garnering intense attention. In one technique, a prosthetic valve is configured to be implanted in a much less invasive procedure by way of catheterization. For instance, U.S. Pat. No. 5,411,552 to Andersen et al. describes a collapsible valve percutaneously introduced in a compressed state through a catheter and expanded in the desired position by balloon inflation. Although these remote implantation techniques have shown great promise for treating certain patients, replacing a valve via surgical intervention is still the preferred treatment procedure. One hurdle to the acceptance of remote implantation is resistance from doctors who are understandably anxious about converting from an effective, if imperfect, regimen to a novel approach that promises great outcomes but is relatively foreign. In conjunction with the understandable caution exercised by surgeons in switching to new techniques of heart valve replacement, regulatory bodies around the world are moving slowly as well. Numerous successful clinical trials and follow-up studies are in process, but much more experience with these new technologies will be required before they are completely accepted.

Accordingly, there is a need for an improved device and associated method of use wherein a prosthetic valve can be surgically implanted in a body channel in a more efficient procedure that reduces the time required on extracorporeal circulation. It is desirable that such a device and method be capable of helping patients with defective valves that are deemed inoperable because their condition is too frail to withstand a lengthy conventional surgical procedure. The present invention addresses these needs and others.

SUMMARY OF THE INVENTION

Various embodiments of the present application provide prosthetic valves and methods of use for replacing a defective native valve in a human heart. Certain embodiments are particularly well adapted for use in a surgical procedure for quickly and easily replacing a heart valve while minimizing time using extracorporeal circulation (i.e., bypass pump).

In one embodiment, a method for treating a native aortic valve in a human heart to replaces the function of the aortic valve, comprises: 1) accessing a native valve through an opening in a chest; 2) advancing an expandable base stent to the site of a native aortic valve, the base stent being radially compressed during the advancement; 3) radially expanding the base stent at the site of the native aortic valve; 4) advancing a valve component within a lumen of the base stent; and 5) expanding a coupling stent on the valve component to mechanically couple to the base stent in a quick and efficient manner.

In one variation, the base stent may comprise a metallic frame. In one embodiment, at least a portion of the metallic frame is made of stainless steel. In another embodiment, at least a portion of the metallic frame is made of a shape memory material. The valve member may take a variety of forms. In one preferred embodiment, the valve component comprises biological tissue. In another variation of this method, the metallic frame is viewed under fluoroscopy during advancement of the prosthetic valve toward the native aortic valve.

The native valve leaflets may be removed before delivering the prosthetic valve. Alternatively, the native leaflets may be left in place to reduce surgery time and to provide a stable base for fixing the base stent within the native valve. In one advantage of this method, the native leaflets recoil inward to enhance the fixation of the metallic frame in the body channel. When the native leaflets are left in place, a balloon or other expansion member may be used to push the valve leaflets out of the way and thereby dilate the native valve before implantation of the base stent. The native annulus may be dilated between 1.5-5 mm from their initial orifice size to accommodate a larger sized prosthetic valve.

In accordance with a preferred aspect, a prosthetic heart valve system comprises a base stent adapted to anchor against a heart valve annulus and defining an orifice therein, and a valve component connected to the base stent. The valve component includes a prosthetic valve defining therein a non-expandable, non-collapsible orifice, and an expandable coupling stent extending from an inflow end thereof. The coupling stent has a contracted state for delivery to an implant position and an expanded state configured for outward connection to the base stent. The base stent may also be expandable with a contracted state for delivery to an implant position adjacent a heart valve annulus and an expanded state sized to contact and anchor against the heart valve annulus. Desirably, the base stent and also the coupling stent are plastically expandable.

In one embodiment, the prosthetic valve comprises a commercially available valve having a sewing ring, and the coupling stent attaches to the sewing ring. The contracted state of the coupling stent may be conical, tapering down in a distal direction. The coupling stent preferably comprises a plurality of radially expandable struts at least some of which are arranged in rows, wherein the distalmost row has the greatest capacity for expansion from the contracted state to the expanded state. Still further, the strut row farthest from the prosthetic valve has alternating peaks and valleys, wherein the base stent includes apertures into which the peaks of the coupling stent may project to interlock the two stents. The base stent may include a plurality of radially expandable struts between axially-oriented struts, wherein at least some of the axially-oriented struts have upper projections that demark locations around the stent.

A method of delivery and implant of a prosthetic heart valve system is also disclosed herein, comprising the steps of:

advancing a base stent to an implant position adjacent a heart valve annulus;

anchoring the base stent to the heart valve annulus;

providing a valve component including a prosthetic valve having a non-expandable, non-collapsible orifice, the valve component further including an expandable coupling stent extending from an inflow end thereof, the coupling stent having a contracted state for delivery to an implant position and an expanded state configured for outward connection to the base stent;

advancing the valve component with the coupling stent in its contracted state to an implant position adjacent the base stent; and expanding the coupling stent to the expanded state in contact with and connected to the base stent.

The base stent may be plastically expandable, and the method further comprises advancing the expandable base stent in a contracted state to the implant position, and plastically expanding the base stent to an expanded state in contact with and anchored to the heart valve annulus, in the process increasing the orifice size of the heart valve annulus by at least 10%, or by 1.5-5 mm. Desirably, the prosthetic valve of the valve component is selected to have an orifice size that matches the increased orifice size of the heart valve annulus. The method may also include mounting the base stent over a mechanical expander, and deploying the base stent at the heart valve annulus using the mechanical expander.

One embodiment of the method further includes mounting the valve component on a holder having a proximal hub and lumen therethrough. The holder mounts on the distal end of a handle having a lumen therethrough, and the method including passing a balloon catheter through the lumen of the handle and the holder and within the valve component, and inflating a balloon on the balloon catheter to expand the coupling stent. The valve component mounted on the holder may be packaged separately from the handle and the balloon catheter. Desirably, the contracted state of the coupling stent is conical, and the balloon on the balloon catheter has a larger distal expanded end than its proximal expanded end so as to apply greater expansion deflection to the coupling stent than to the prosthetic valve.

In the method where the coupling stent is conical, the coupling stent may comprise a plurality of radially expandable struts at least some of which are arranged in rows, wherein the row farthest from the prosthetic valve has the greatest capacity for expansion from the contracted state to the expanded state.

The method may employ a coupling stent with a plurality of radially expandable struts, wherein a row farthest from the prosthetic valve has alternating peaks and valleys. The distal end of the coupling stent thus expands more than the rest of the coupling stent so that the peaks in the row farthest from the prosthetic valve project outward into apertures in the base stent. Both the base stent and the coupling stent may have a plurality of radially expandable struts between axially-oriented struts, wherein the method includes orienting the coupling stent so that its axially-oriented struts are out of phase with those of the base stent to increase retention therebetween.

Another aspect described herein is a system for delivering a valve component including a prosthetic valve having a non-expandable, non-collapsible orifice, and an expandable coupling stent extending from an inflow end thereof, the coupling stent having a contracted state for delivery to an implant position and an expanded state. The delivery system includes a valve holder connected to a proximal end of the valve component, a balloon catheter having a balloon, and a handle configured to attach to a proximal end of the valve holder and having a lumen for passage of the catheter, wherein the balloon extends distally through the handle, past the holder and through the valve component. In the system, the prosthetic valve is preferably a commercially available valve having a sewing ring to which the coupling stent attaches.

The contracted state of the coupling stent in the delivery system may be conical, tapering down in a distal direction. Furthermore, the balloon catheter further may include a generally conical nose cone on a distal end thereof that extends through the valve component and engages a distal end of the coupling stent in its contracted state. Desirably, the handle comprises a proximal section and a distal section that may be coupled together in series to form a continuous lumen, wherein the distal section is adapted to couple to the hub of the holder to enable manual manipulation of the valve component using the distal section prior to connection with the proximal handle section. Preferably, the balloon catheter and proximal handle section are packaged together with the balloon within the proximal section lumen.

Alternatively, the valve component mounted on the holder may be packaged separately from the handle and the balloon catheter.

A further understanding of the nature and advantages of the present invention are set forth in the following description and claims, particularly when considered in conjunction with the accompanying drawings in which like parts bear like reference numerals.

BRIEF DESCRIPTION OF THE DRAWINGS

The invention will now be explained and other advantages and features will appear with reference to the accompanying schematic drawings wherein:

FIGS. 5A-5H are sectional views through an isolated aortic annulus showing a portion of the adjacent left ventricle and aorta, and illustrating a number of steps in deployment of an exemplary prosthetic heart valve system of the present invention;

FIG. 5A shows a deflated balloon catheter having a base stent thereon advanced into position at the aortic annulus;

FIG. 5B shows the balloon on the catheter inflated to expand and deploy the base stent against the aortic annulus;

FIG. 5C shows the deployed base stent in position within the aortic annulus;

FIG. 5D shows a valve component mounted on a balloon catheter advancing into position within the base stent;

FIG. 5E shows the valve component in a desired implant position at the aortic annulus and within the base stent, with the balloon catheter advanced farther to displace a nose cone out of engagement with a coupling stent;

FIG. 5F shows the balloon on the catheter inflated to expand and deploy a valve component coupling stent against the base stent;

FIG. 5G shows the deflated balloon on the catheter along with the nose cone being removed from within the valve component;

FIG. 5H shows the fully deployed prosthetic heart valve of the present invention;

FIG. 6 is an exploded view of an exemplary system for delivering the prosthetic heart valve of the present invention;

FIG. 7 is an assembled view of the delivery system of FIG. 6 showing a nose cone extending over a distal end of a valve component coupling stent;

FIG. 8 is a view like FIG. 7 but with a balloon catheter displaced distally to disengage the nose cone from the coupling stent;

FIG. 9 is an assembled view of the delivery system similar to that shown in FIG. 7 and showing a balloon inflated to expand the valve component coupling stent;

FIG. 10 is an exploded elevational view of several components of the introducing system of FIG. 9, without the balloon catheter, valve component and holder;

FIG. 14-17 are plan views of a still further alternative coupling stent;

FIG. 18A-18B are flat and tubular views of an exemplary base stent with upper position markers and a phantom coupling stent superimposed thereover;

FIG. 19 is a flat view of an alternative base stent with a coupling stent superimposed thereover;

FIG. 20 is a sectional view of a coupling stent within a base stent illustrating one method of interlocking.

DETAILED DESCRIPTION OF THE PREFERRED EMBODIMENTS

Figure 1:
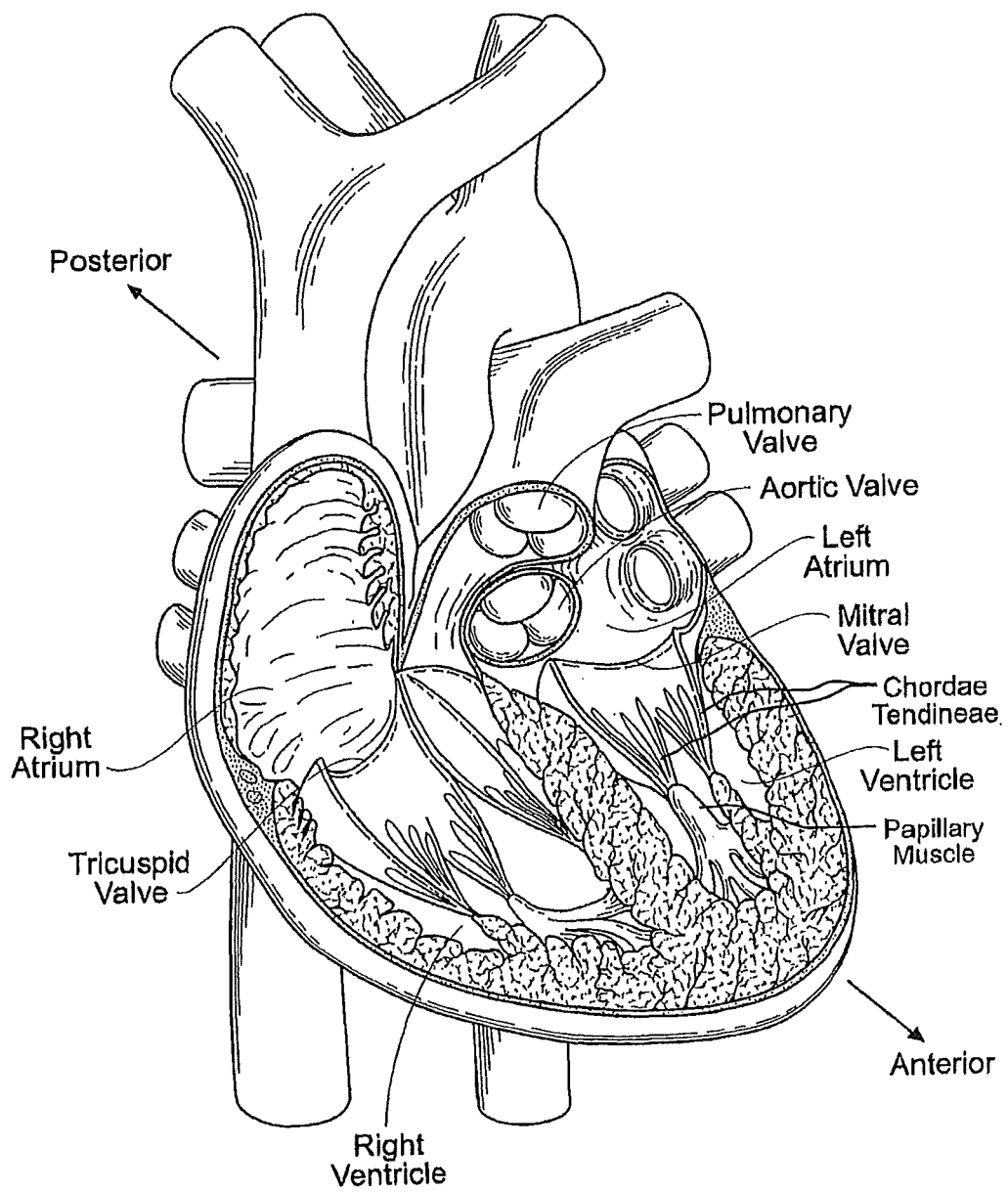
FIG. 1 is an anatomic anterior view of a human heart, with portions broken away and in section to view the interior heart chambers and adjacent structures.
Figure 2:
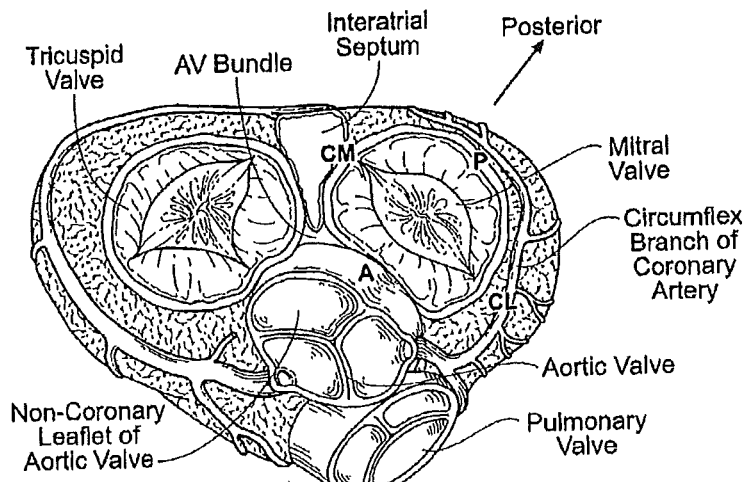
FIG. 2 is an anatomic superior view of a section of the human heart showing the tricuspid valve in the right atrium, the mitral valve in the left atrium, and the aortic valve in between, with the tricuspid and mitral valves open and the aortic and pulmonary valves closed during ventricular diastole (ventricular filling) of the cardiac cycle.
Figure 4:
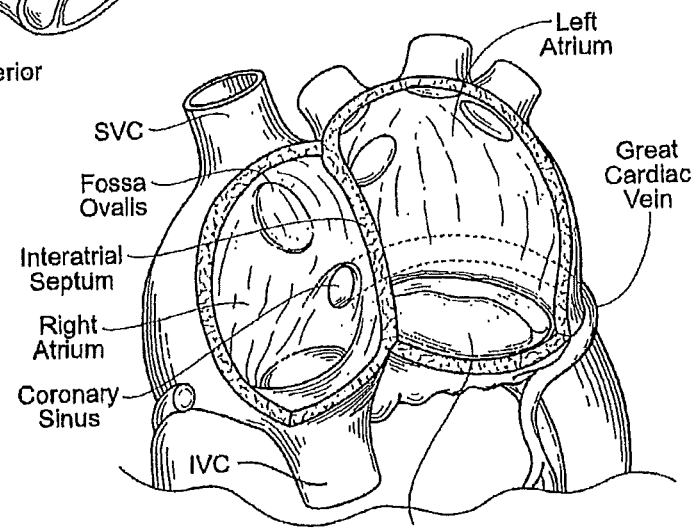
FIG. 4 is an anatomic anterior perspective view of the left and right atria, with portions broken away and in section to show the interior of the heart chambers and associated structures, such as the fossa ovalis, coronary sinus, and the great cardiac vein.
Figure 3:
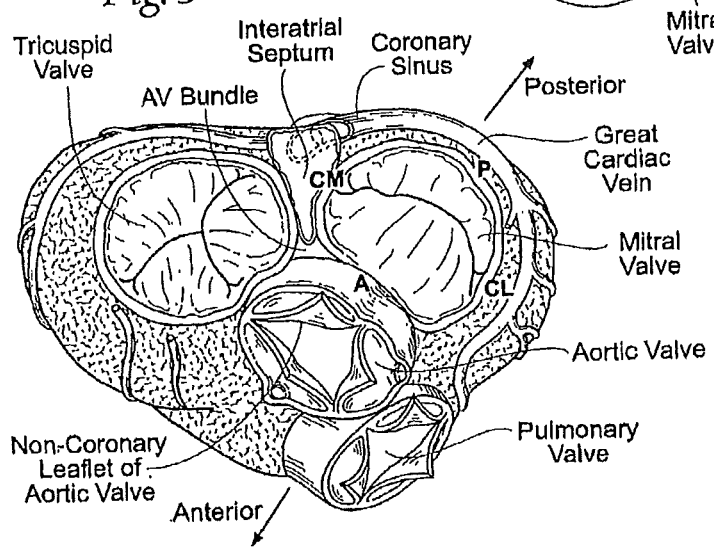
FIG. 3 is an anatomic superior view of a section of the human heart shown in FIG. 2, with the tricuspid and mitral valves closed and the aortic and pulmonary valves opened during ventricular systole (ventricular emptying) of the cardiac cycle.

The present invention attempts to overcome drawbacks associated with conventional, open-heart surgery, while also adopting some of the techniques of newer technologies which decrease the duration of the treatment procedure. The prosthetic heart valves of the present invention are primarily intended to be delivered and implanted using conventional surgical techniques, including the aforementioned open-heart surgery. There are a number of approaches in such surgeries, all of which result in the formation of a direct access pathway to the particular heart valve annulus. For clarification, a direct access pathway is one that permits direct (i.e., naked eye) visualization of the heart valve annulus. In addition, it will be recognized that embodiments of the two-stage prosthetic heart valves described herein may also be configured for delivery using percutaneous approaches, and those minimally-invasive surgical approaches that require remote implantation of the valve using indirect visualization.

One primary aspect of the present invention is a two-stage prosthetic heart valve wherein the tasks of implanting a tissue anchor first and then a valve member are distinct and certain advantages result. The exemplary two-stage prosthetic heart valve of the present invention has an expandable base stent secured to tissue in the appropriate location using a balloon or other expansion technique. A hybrid valve member that has non-expandable and expandable portions then couples to the base stent in a separate or sequential operation. By utilizing an expandable base stent, the duration of the initial anchoring operation is greatly reduced as compared with a conventional sewing procedure utilizing an array of sutures. The expandable base stent may simply be radially expanded outward into contact with the implantation site, or may be provided with additional anchoring means, such as barbs. The operation may be carried out using a conventional open-heart approach and cardiopulmonary bypass. In one advantageous feature, the time on bypass is greatly reduced due to the relative speed of implanting the expandable base stent.

For definitional purposes, the term "base stent," refers to a structural component of a heart valve that is capable of attaching to tissue of a heart valve annulus. The base stents described herein are most typically tubular stents, or stents having varying shapes or diameters. A stent is normally formed of a biocompatible metal wire frame, such as stainless steel or Nitinol. Other base stents that could be used with valves of the present invention include rigid rings, spirally-wound tubes, and other such tubes that fit tightly within a valve annulus and define an orifice therethrough for the passage of blood, or within which a valve member is mounted. It is entirely conceivable, however, that the base stent could be separate clamps or hooks that do not define a continuous periphery. Although such devices sacrifice some dynamic stability, and speed and ease of deployment, these devices could be configured to work in conjunction with a particular valve member.

A distinction between self-expanding and balloon-expanding stents exists in the field. A self-expanding stent may be crimped or otherwise compressed into a small tube and possesses sufficient elasticity to spring outward by itself when a restraint such as an outer sheath is removed. In contrast, a balloon-expanding stent is made of a material that is substantially less elastic, and indeed must be plastically expanded from the inside out when converting from a compressed diameter to an expanded. It should be understood that the term balloon-expanding stents encompasses plastically-expandable stents, whether or not a balloon is used to actually expand it. The material of the stent plastically deforms after application of a deformation force such as an inflating balloon or expanding mechanical fingers. Both alternatives will be described below. Consequently, the term "balloon-expandable stent" should be considered to refer to the material or type of the stent as opposed to the specific expansion means.

The term "valve member" refers to that component of a heart valve that possesses the fluid occluding surfaces to prevent blood flow in one direction while permitting it in another. As mentioned above, various constructions of valve members are available, including those with flexible leaflets and those with rigid leaflets or a ball and cage arrangement. The leaflets may be bioprosthetic, synthetic, or metallic.

A primary focus of the present invention is a two-stage prosthetic heart valve having a first stage in which a base stent secures to a valve annulus, and a subsequent second stage in which a valve member connects to the base stent. It should be noted that these stages can be done almost simultaneously, such as if the two components were mounted on the same delivery device, or can be done in two separate clinical steps, with the base stent deployed using a first delivery device, and then the valve member using another delivery device. It should also be noted that the term "two-stage" refers to the two primary steps of anchoring structure to the annulus and then connecting a valve member, which does not necessarily limit the valve to just two parts.

Another potential benefit of a two-stage prosthetic heart valve, including a base stent and a valve member, is that the valve member may be replaced after implantation without replacing the base stent. That is, an easily detachable means for coupling the valve member and base stent may be used that permits a new valve member to be implanted with relative ease. Various configurations for coupling the valve member and base stent are described herein.

It should be understood, therefore, that certain benefits of the invention are independent of whether the base stent is expandable or not. That is, various embodiments illustrate an expandable base stent coupled to a hybrid valve member that has non-expandable and expandable portions. However, the same coupling structure may be utilized for a non-expandable base stent and hybrid valve member. Therefore, the invention should be interpreted via the appended claims.

As a point of further definition, the term "expandable" is used herein to refer to a component of the heart valve capable of expanding from a first, delivery diameter to a second, implantation diameter. An expandable structure, therefore, does not mean one that might undergo slight expansion from a rise in temperature, or other such incidental cause. Conversely, "non-expandable" should not be interpreted to mean completely rigid or a dimensionally stable, as some slight expansion of conventional "non-expandable" heart valves, for example, may be observed.

In the description that follows, the term "body channel" is used to define a blood conduit or vessel within the body. Of course, the particular application of the prosthetic heart valve determines the body channel at issue. An aortic valve replacement, for example, would be implanted in, or adjacent to, the aortic annulus. Likewise, a mitral valve replacement will be implanted at the mitral annulus. Certain features of the present invention are particularly advantageous for one implantation site or the other. However, unless the combination is structurally impossible, or excluded by claim language, any of the heart valve embodiments described herein could be implanted in any body channel.

FIGS. 5A-5H are sectional views through an isolated aortic annulus AA showing a portion of the adjacent left ventricle LV and ascending aorta with sinus cavities S. The two coronary sinuses CS are also shown. The series of views show snapshots of a number of steps in deployment of an exemplary prosthetic heart valve system of the present invention, which comprises a two-component system. A first component is a base stent that is deployed against the native leaflets or, if the leaflets are excised, against the debrided aortic annulus AA. A second valve component fits within the base stent and anchors thereto. Although two-part valves are known in the art, this is believed to be the first that utilizes a stent within a stent in conjunction with a non-expandable valve.

FIG. 5A shows a catheter 20 having a balloon 22 in a deflated state near a distal end with a tubular base stent 24 crimped thereover. The stent 24 is shown in a radially constricted, undeployed configuration. The catheter 20 has been advanced to position the base stent 24 so that it is approximately axially centered at the aortic annulus AA.

FIG. 5B shows the balloon 22 on the catheter 20 inflated to expand and deploy the base stent 24 against the aortic annulus AA, and FIG. 5C shows the deployed base stent in position after deflation of the balloon 22 and removal of the catheter 20. The stent 24 provides a base within and against a body lumen (e.g., a valve annulus). Although a stent is described for purposes of illustration, any member capable of anchoring within and against the body lumen and then coupling to the valve component may be used. In a preferred embodiment, the base stent 24 comprises a plastically-expandable cloth-covered stainless-steel tubular stent. One advantage of using a plastically-expandable stent is the ability to expand the native annulus to receive a larger valve size than would otherwise be possible with conventional surgery. Desirably, the left ventricular outflow tract (LVOT) is significantly expanded by at least 10%, or for example by 1.5-5 mm, and the surgeon can select a valve component 30 with a larger orifice diameter relative to an unexpanded annulus. On the other hand, the present invention could also use a self-expanding base stent 24 which is then reinforced by the subsequently implanted valve component 30. Because the valve component 30 has a non-compressible part, the prosthetic valve 34, and desirably a plastically-expandable coupling stent 36, it effectively resists recoil of the self-expanded base stent 24.

With continued reference to FIG. 5B, the stent 24 has a diameter sized to be deployed at the location of the native valve (e.g., along the aortic annulus). A portion of the stent 24 may expand outwardly into the respective cavity adjacent the native valve. For example, in an aortic valve replacement, an upper portion may expand into the area of the sinus cavities just downstream from the aortic annulus. Of course, care should be taken to orient the stent 24 so as not to block the coronary openings. The stent body is preferably configured with sufficient radial strength for pushing aside the native leaflets and holding the native leaflets open in a dilated condition. The native leaflets provide a stable base for holding the stent, thereby helping to securely anchor the stent in the body. To further secure the stent to the surrounding tissue, the lower portion may be configured with anchoring members, such as, for example, hooks or barbs (not shown).

As will be described in more detail below, the prosthetic valve system includes a valve component that may be quickly and easily connected to the stent 24. It should be noted here that the base stents described herein can be a variety of designs, including having the diamond/chevron-shaped openings shown or other configurations. The material depends on the mode of delivery (i.e., balloon- or self-expanding), and the stent can be bare strut material or covered to promote ingrowth and/or to reduce paravalvular leakage. For example, a suitable cover that is often used is a sleeve of fabric such as Dacron.

One primary advantage of the prosthetic heart valve system of the present invention is the speed of deployment. Therefore, the base stent 24 may take a number of different configurations as long as it does not require the time-consuming process of suturing it to the annulus. For instance, another possible configuration for the base stent 24 is one that is not fully expandable like the tubular stent as shown. That is, the base stent 24 may have a non-expandable ring-shaped orifice from which an expandable skirt stent or series of anchoring barbs deploy.

FIG. 5D shows a valve component 30 mounted on a balloon catheter 32 advancing into position within the base stent 24. The valve component 30 comprises a prosthetic valve 34 and a coupling stent 36 attached to and projecting from a distal end thereof. In its radially constricted or undeployed state, the coupling stent 36 assumes a conical inward taper in the distal direction. The catheter 32 extends through the valve component 30 and terminates in a distal nose cone 38 which has a conical or bell-shape and covers the tapered distal end of the coupling stent 36. Although not shown, the catheter 32 extends through an introducing cannula and valve holder.

When used for aortic valve replacement, the prosthetic valve 34 preferably has three flexible leaflets which provide the fluid occluding surfaces to replace the function of the native valve leaflets. In various preferred embodiments, the valve leaflets may be taken from another human heart (cadaver), a cow (bovine), a pig (porcine valve) or a horse (equine). In other preferred variations, the valve member may comprise mechanical components rather than biological tissue. The three leaflets are supported by three commissural posts. A ring is provided along the base portion of the valve member.

In a preferred embodiment, the prosthetic valve 34 partly comprises a commercially available, non-expandable prosthetic heart valve, such as the Carpentier-Edwards PERIMOUNT Magna® Aortic Heart Valve available from Edwards Lifesciences of Irvine, Calif. In this sense, a "commercially available" prosthetic heart valve is an off-the-shelf (i.e., suitable for stand-alone sale and use) prosthetic heart valve defining therein a non-expandable, non-collapsible orifice and having a sewing ring capable of being implanted using sutures through the sewing ring in an open-heart, surgical procedure. The particular approach into the heart used may differ, but in surgical procedures the heart is stopped and opened, in contrast to beating heart procedures where the heart remains functional. To reiterate, the terms "non-expandable" and "non-collapsible" should not be interpreted to mean completely rigid and dimensionally stable, merely that the valve is not expandable/collapsible like some proposed minimally-invasively or percutaneously-delivered valves.

An implant procedure therefore involves first delivering and expanding the base stent 24 at the aortic annulus, and then coupling the valve component 30 including the valve 34 thereto. Because the valve 34 is non-expandable, the entire procedure is typically done using the conventional open-heart technique. However, because the base stent 24 is delivered and implanted by simple expansion, and then the valve component 30 attached thereto by expansion, both without suturing, the entire operation takes less time. This hybrid approach will also be much more comfortable to surgeons familiar with the open-heart procedures and commercially available heart valves.

Moreover, the relatively small change in procedure coupled with the use of proven heart valves should create a much easier regulatory path than strictly expandable, remote procedures. Even if the system must be validated through clinical testing to satisfy the Pre-Market Approval (PMA) process with the FDA (as opposed to a 510k submission), the acceptance of the valve component 30 at least will be greatly streamlined with a commercial heart valve that is already approved, such as the Magna® Aortic Heart Valve.

The prosthetic valve 34 is provided with an expandable coupling mechanism in the form of the coupling stent 36 for securing the valve to the base stent 24. Although the coupling stent 36 is shown, the coupling mechanism may take a variety of different forms, but eliminates the need for connecting sutures and provides a rapid connection means.

Figure 5E:
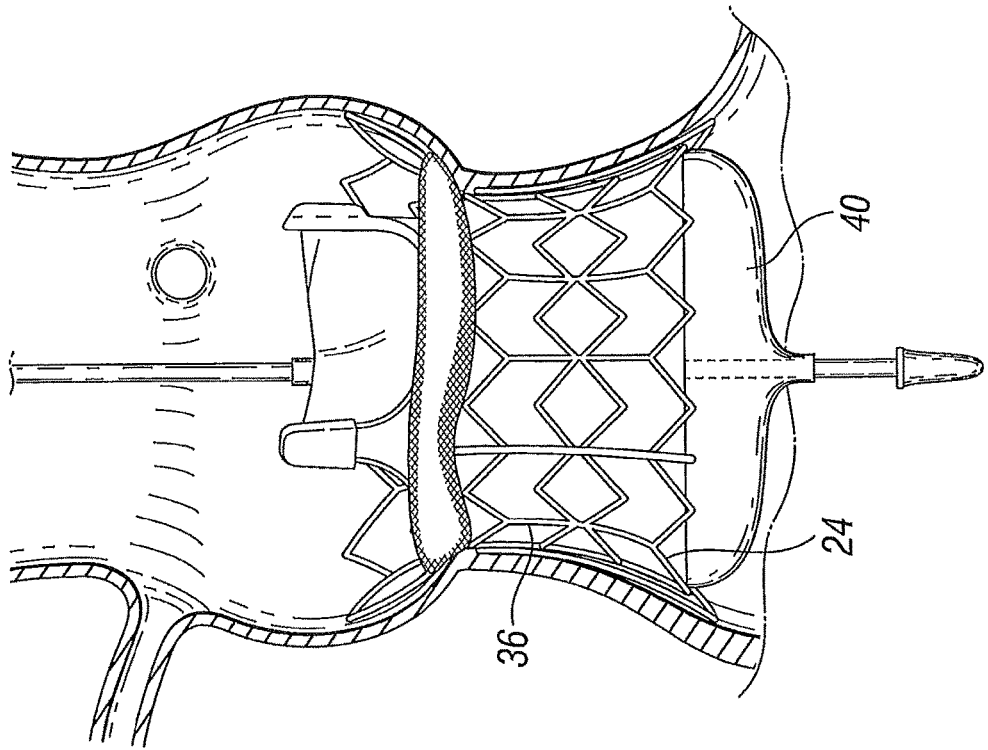

In FIG. 5E the valve component 30 has advanced to a desired implant position at the aortic annulus AA and within the base stent 24. The prosthetic valve 34 may include a suture-permeable ring 42 that desirably abuts the aortic annulus AA. More preferably, the sewing ring 42 is positioned supra-annularly, or above the narrowest point of the aortic annulus AA, so as to allow selection of a larger orifice size than a valve placed intra-annularly. With the aforementioned annulus expansion using the base stent 24, and the supra-annular placement, the surgeon may select a valve having a size one or two increments larger than previously conceivable. As mentioned, the prosthetic valve 34 is desirably a commercially available heart valve having a sewing ring 42. The balloon catheter 32 has advanced relative to the valve component 30 to displace the nose cone 38 out of engagement with the coupling stent 36. A dilatation balloon 40 on the catheter 30 can be seen just beyond the distal end of the coupling stent 36.

Figure 5F:
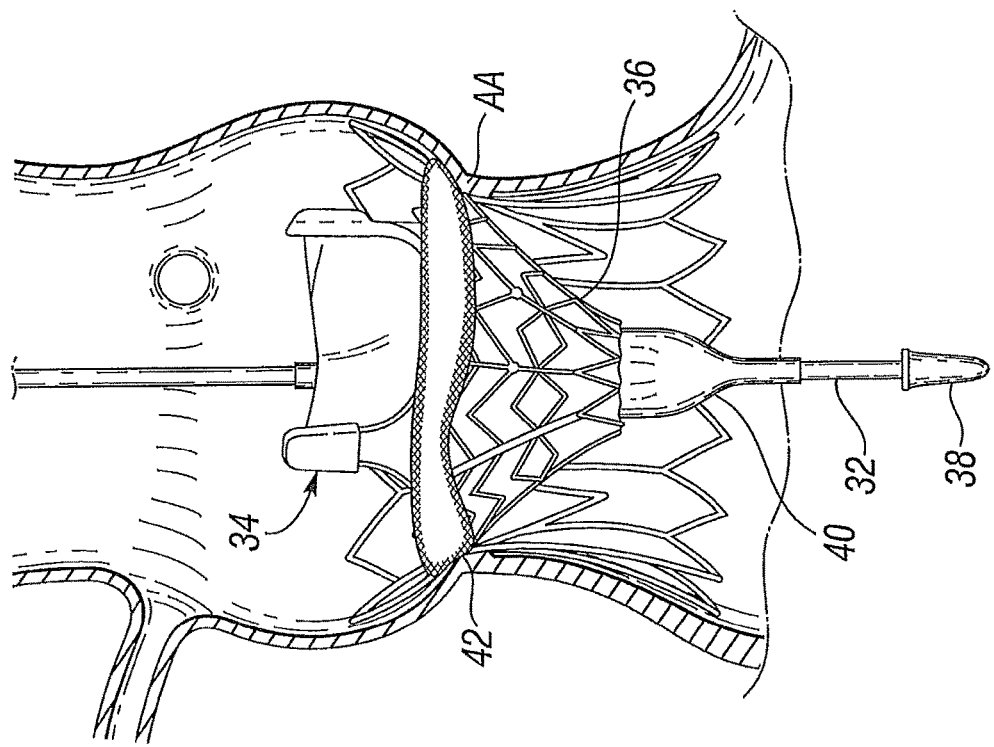

FIG. 5F shows the balloon 40 on the catheter 32 inflated to expand and deploy the coupling stent 36 against the base stent 24. The balloon 40 is desirably inflated using controlled, pressurized, sterile physiologic saline. The coupling stent 36 transitions between its conical contracted state and its generally tubular expanded state. Simple interference between the coupling stent 36 and the base stent 24 may be sufficient to anchor the valve component 30 within the base stent, or interacting features such as projections, hooks, barbs, fabric, etc. may be utilized.

Because the base stent 24 expands before the valve component 30 attaches thereto, a higher strength stent (self- or balloon-expandable) configuration may be used. For instance, a relatively robust base stent 24 may be used to push the native leaflets aside, and the absent valve component 30 is not damaged or otherwise adversely affected during the high-pressure base stent deployment. After the base stent 24 deploys in the body channel, the valve component 30 connects thereto by deploying the coupling stent 36, which may be somewhat more lightweight requiring smaller expansion forces. Also, the balloon 40 may have a larger distal expanded end than its proximal expanded end so as to apply more force to the coupling stent 36 than to the prosthetic valve 34. In this way, the prosthetic valve 34 and flexible leaflets therein are not subject to high expansion forces from the balloon 40. Indeed, although balloon deployment is shown, the coupling stent 36 may also be a self-expanding type of stent. In the latter configuration, the nose cone 38 is adapted to retain the coupling stent 36 in its constricted state prior to position in the valve component 30 within the base stent 24.

As noted above, the base stents described herein could include barbs or other tissue anchors to further secure the stent to the tissue, or to secure the coupling stent 36 to the base stent 24. Further, the barbs could be deployable (e.g., configured to extend or be pushed radially outward) by the expansion of a balloon. Preferably, the coupling stent 36 is covered to promote in-growth and/or to reduce paravalvular leakage, such as with a Dacron tube or the like.

Figure 5H:
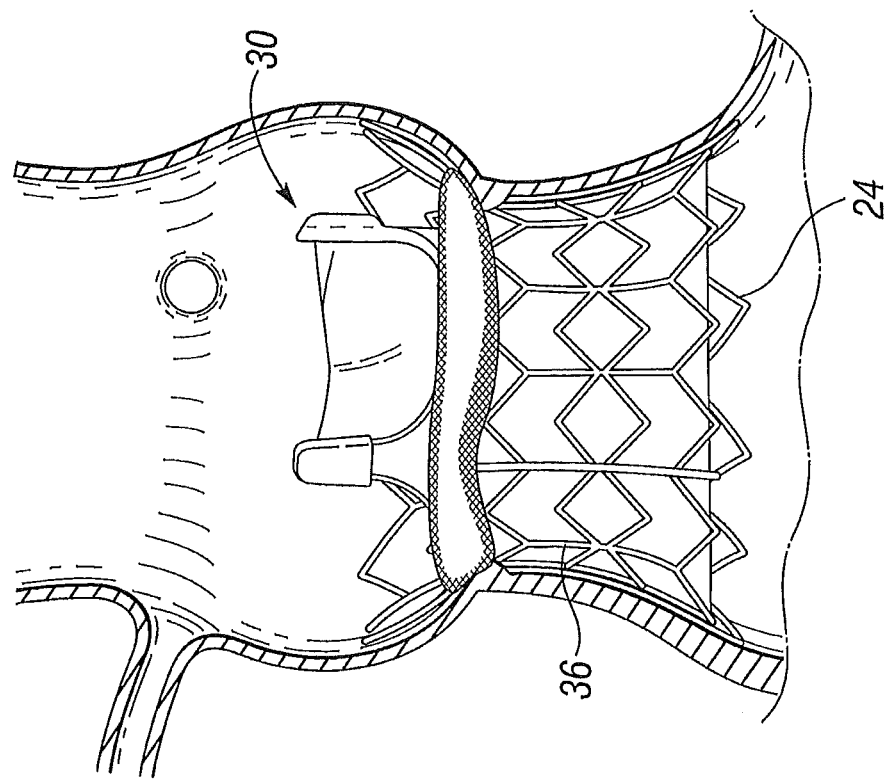
Figure 5G:
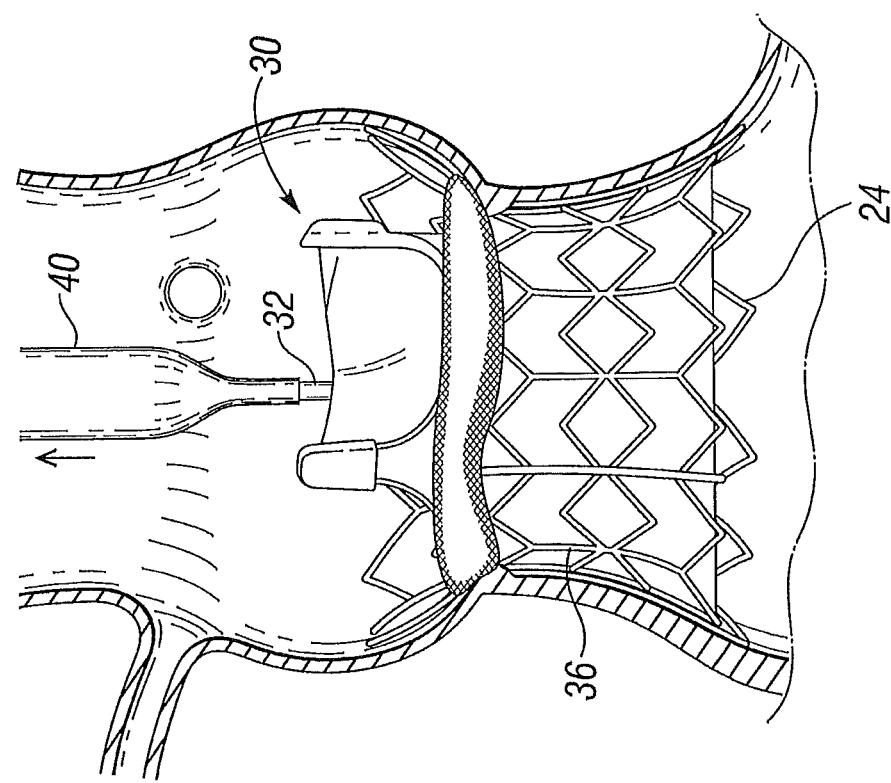

FIG. 5G shows the deflated balloon 40 on the catheter 32 along with the nose cone 38 being removed from within the valve component 30. Finally, FIG. 5H shows the fully deployed prosthetic heart valve system of the present invention including the valve component 30 coupled to the base stent 24 within the aortic annulus AA.

FIG. 6 is an exploded view, and FIGS. 7 and 8 are assembled views, of an exemplary system 50 for delivering the prosthetic heart valve of the present invention. Modified components of the delivery system 50 are also shown in FIGS. 9 and 10. The delivery system 50 includes a balloon catheter 52 having the balloon 40 on its distal end and an obturator 54 on a proximal end. The obturator 54 presents a proximal coupling 56 that receives a luer connector or other such fastener of a Y-fitting 58. The aforementioned nose cone 38 may attach to the distalmost end of the catheter 52, but more preferably attaches to a wire (not shown) inserted through the center lumen of the balloon catheter 52.

The catheter 52 and the nose cone 38 pass through a hollow handle 60 having a proximal section 62 and a distal section 64. A distal end of the distal handle section 64 firmly attaches to a hub 66 of a valve holder 68, which in turn attaches to the prosthetic heart valve component 30. Details of the valve holder 68 will be given below with reference to FIGS. 11A-11E.

The two sections 62, 64 of the handle 60 are desirably formed of a rigid material, such as a molded plastic, and coupled to one another to form a relatively rigid and elongated tube for manipulating the prosthetic valve component 30 attached to its distal end. In particular, the distal section 64 may be easily coupled to the holder hub 66 and therefore provide a convenient tool for managing the valve component 30 during pre-surgical rinsing steps. For this purpose, the distal section 64 features a distal tubular segment 70 that couples to the holder hub 66, and an enlarged proximal segment 72 having an opening on its proximal end that receives a tubular extension 74 of the proximal handle section 62. FIG. 6 shows an O-ring 76 that may be provided on the exterior of the tubular extension 74 for a frictional interference fit to prevent the two sections from disengaging. Although not shown, the distal tubular segment 70 may also have an O-ring for firmly coupling to the holder hub 66, or may be attached with threading or the like. In one preferred embodiment, the balloon 40 on the catheter 52 is packaged within the proximal handle section 62 for protection and ease of handling. Coupling the proximal and distal handle sections 62, 64 therefore "loads" the system 50 such that the balloon catheter 52 may be advanced through the continuous lumen leading to the valve component 30.

FIGS. 9 and 10 illustrate a delivery system 50 similar to that shown in FIG. 7, but with alternative couplers 77 on both the proximal and distal handle sections 62, 64 in the form of cantilevered teeth that snap into complementary recesses formed in the respective receiving apertures. Likewise, threading on the mating parts could also be used, as well as other similar expedients. FIG. 9 shows the balloon 40 inflated to expand the valve component coupling stent 36.

In a preferred embodiment, the prosthetic valve component 30 incorporates bioprosthetic tissue leaflets and is packaged and stored attached to the holder 68 but separate from the other introduction system 50 components. Typically, bioprosthetic tissue is packaged and stored in a jar with preservative solution for long shelf life, while the other components are packaged and stored dry.

When assembled as seen in FIGS. 7-9, an elongated lumen (not numbered) extends from the proximal end of the Y-fitting 58 to the interior of the balloon 40. The Y-fitting 58 desirably includes an internally threaded connector 80 for attachment to an insufflation system, or a side port 82 having a luer fitting 84 or similar expedient may be used for insufflation of the balloon 40.

FIGS. 7 and 8 show two longitudinal positions of the catheter 52 and associated structures relative to the handle 60 and its associated structures. In a retracted position shown in FIG. 7, the balloon 40 primarily resides within the distal handle section 64. FIG. 7 illustrates the delivery configuration of the introduction system 50, in which the surgeon advances the prosthetic valve component 30 from outside the body into a location adjacent the target annulus. The nose cone 38 extends around and protects a distal end of the conical undeployed coupling stent 36. This configuration is also seen in FIG. 5D, albeit with the holder 68 removed for clarity. Note the spacing S between the proximal coupling 56 and the proximal end of the handle 60.

As explained above with respect to FIGS. 5A-5H, the surgeon advances the prosthetic valve component 30 into its desired implantation position at the valve annulus, and then advances the balloon 40 through the valve component and inflates it. To do so, the operator converts the delivery system 50 from the retracted configuration of FIG. 7 to the deployment configuration of FIG. 8, with the balloon catheter 40 displaced distally as indicated by the arrow 78 to disengage the nose cone 38 from the coupling stent 36. Note that the proximal coupling 56 now contacts the proximal end of the handle 60, eliminating the space S indicated in FIG. 7.

It should be understood that the prosthetic valve component 30 may be implanted at the valve annulus with a pre-deployed base stent 24, as explained above, or without. The coupling stent 36 may be robust enough to anchor the valve component 30 directly against the native annulus (with or without leaflet excision) in the absence of the base stent 24. Consequently, the description of the system 50 for introducing the prosthetic heart valve should be understood in the context of operating with or without the pre-deployed base stent 24.

Figure 11A:
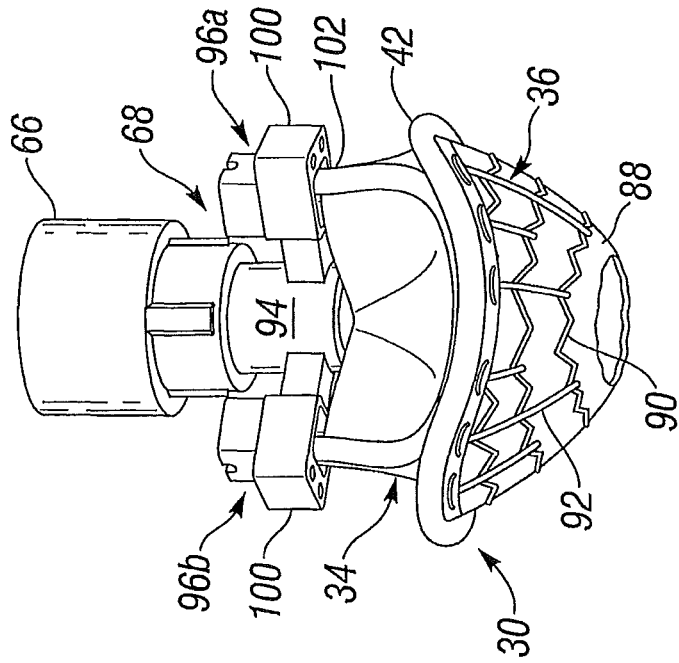
FIGS. 11A and 11B are perspective views of an exemplary valve component assembled on a valve holder of the present invention.

Prior to a further description of operation of the delivery system 50, a more detailed explanation of the valve component 30 and valve holder 68 is necessary. FIGS. 11A-11E show a number of perspective and other views of the exemplary valve component 30 mounted on the delivery holder 68 of the present invention. As mentioned, the valve component 30 comprises the prosthetic valve 34 having the coupling stent 36 attached to an inflow end thereof. In a preferred embodiment, the prosthetic valve 34 comprises a commercially available off-the-shelf non-expandable, non-collapsible commercial prosthetic valve. Any number of prosthetic heart valves can be retrofit to attach the coupling stent 36, and thus be suitable for use in the context of the present invention. For example, the prosthetic valve 34 may be a mechanical valve or a valve with flexible leaflets, either synthetic or bioprosthetic. In a preferred embodiment, however, the prosthetic valve 34 includes bioprosthetic tissue leaflets 86 (FIG. 11A). Furthermore, as mentioned above, the prosthetic valve 34 is desirably a Carpentier-Edwards PERIMOUNT Magna® Aortic Heart Valve (e.g., model 3000TFX) available from Edwards Lifesciences of Irvine, Calif.

The coupling stent 36 preferably attaches to the ventricular (or inflow) aspect of the valve's sewing ring 42 during the manufacturing process in a way that preserves the integrity of the sewing ring and prevents reduction of the valve's effective orifice area (EOA). Desirably, the coupling stent 36 will be continuously sutured to sewing ring 42 in a manner that maintains the outer contours of the sewing ring. Sutures may be passed through apertures or eyelets in the stent skeleton, or through a cloth covering that in turn is sewn to the skeleton. Other connection solutions include prongs or hooks extending inward from the stent, ties, Velcro, snaps, adhesives, etc. Alternatively, the coupling stent 36 may be more rigidly connected to rigid components within the prosthetic valve 34. During implant, therefore, the surgeon can seat the sewing ring 42 against the annulus in accordance with a conventional surgery. This gives the surgeon familiar tactile feedback to ensure that the proper patient-prosthesis match has been achieved. Moreover, placement of the sewing ring 42 against the outflow side of the annulus helps reduce the probability of migration of the valve component 30 toward the ventricle.

The coupling stent 36 may be a pre-crimped, tapered, 316L stainless steel balloon-expandable stent, desirably covered by a polyester skirt 88 to help seal against paravalvular leakage and promote tissue ingrowth once implanted within the base stent 24 (see FIG. 5F). The coupling stent 36 transitions between the tapered constricted shape of FIGS. 11A-11E to its flared expanded shape shown in FIG. 5F, and also in FIG. 10.

The coupling stent 36 desirably comprises a plurality of sawtooth-shaped or otherwise angled, serpentine or web-like struts 90 connected to three generally axially-extending posts 92. As will be seen below, the posts 92 desirably feature a series of evenly spaced apertures to which sutures holding the polyester skirt 88 in place may be anchored. As seen best in FIG. 5F, the stent 36 when expanded flares outward and conforms closely against the inner surface of the base stent 24, and has an axial length substantially the same as the base stent. Anchoring devices such as barbs or other protuberances from the coupling stent 36 may be provided to enhance the frictional hold between the coupling stent and the base stent 24.

It should be understood that the particular configuration of the coupling stent, whether possessing straight or curvilinear struts 90, may be modified as needed. There are numerous stent designs, as described below with reference to FIGS. 12-17, any of which potentially may be suitable. Likewise, although the preferred embodiment incorporates a balloon-expandable coupling stent 36, a self-expanding stent could be substituted with certain modifications, primarily to the delivery system. The same flexibility and design of course applies to the base stent 24. In a preferred embodiment, both the base stent 24 and the coupling stent 36 are desirably plastically-expandable to provide a firmer anchor for the valve 34; first to the annulus with or without native leaflets, and then between the two stents. The stents may be expanded using a balloon or mechanical expander as described below.

Still with reference to FIGS. 11A-11E, the holder 68 comprises the aforementioned proximal hub 66 and a thinner distal extension 94 thereof forming a central portion of the holder. Three legs 96a, 96b, 96c circumferentially equidistantly spaced around the central extension 94 and projecting radially outward therefrom comprise inner struts 98 and outer commissure rests 100. The prosthetic valve 34 preferably includes a plurality, typically three, commissures 102 that project in an outflow direction. Although not shown, the commissure rests 100 preferably incorporate depressions into which fit the tips of the commissures 102.

In one embodiment, the holder 68 is formed of a rigid polymer such as Delrin or polypropylene that is transparent to increase visibility of an implant procedure. As best seen in FIG. 11E, the holder 68 exhibits openings between the legs 96a, 96b, 96c to provide a surgeon good visibility of the valve leaflets 86, and the transparency of the legs further facilitates visibility and permits transmission of light therethrough to minimize shadows. Although not described in detail herein, FIG. 11E also illustrate a series of through holes in the legs 96a, 96b, 96c permitting connecting sutures to be passed through fabric in the prosthetic valve 34 and across a cutting guide in each leg. As is known in the art, severing a middle length of suture that is connected to the holder 68 and passes through the valve permits the holder to be pulled free from the valve when desired.

Figure 11B:
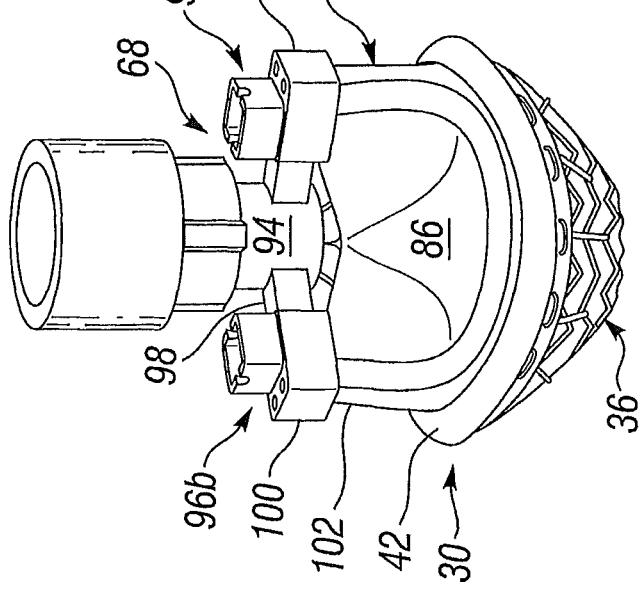
Figure 11E:
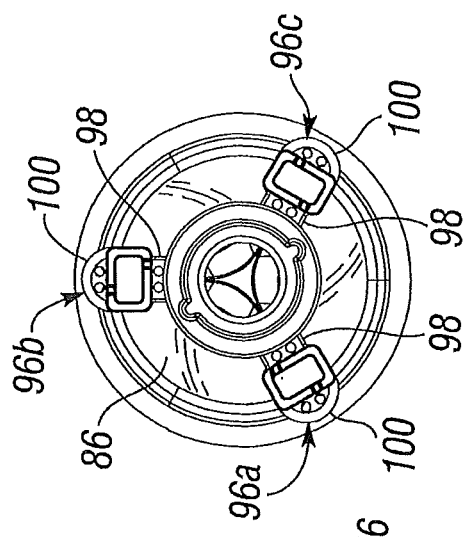
FIGS. 11D and 11E are top and bottom plan views of the assembly of FIGS. 11A and 11B.
Figure 11C:
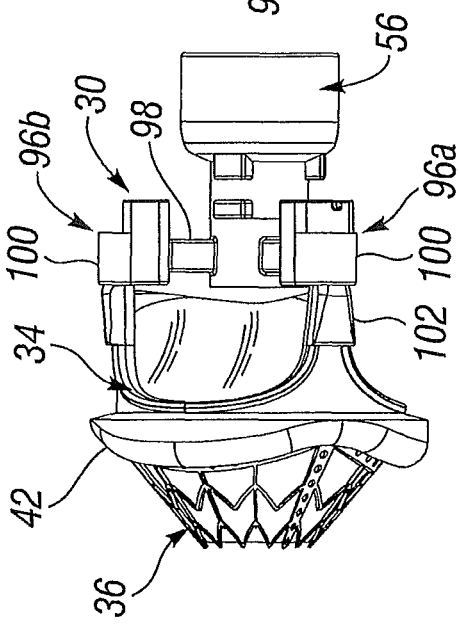
FIG. 11C is a side elevational view of the assembly of FIGS. 11A and 11B.
Figure 11D:
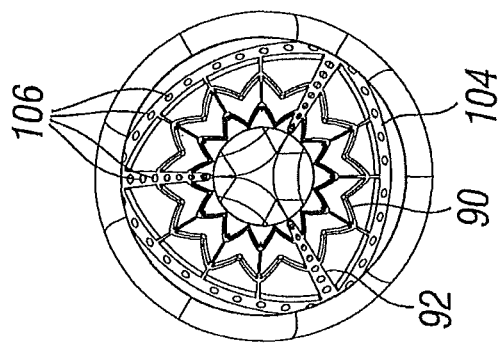

FIGS. 11C and 11D illustrate a somewhat modified coupling stent 36 from that shown in FIGS. 11A and 11B, wherein the struts 90 and axially-extending posts 92 are better defined. Specifically, the posts 92 are somewhat wider and more robust than the struts 90, as the latter provide the stent 36 with the ability to expand from the conical shape shown to a more tubular configuration. Also, a generally circular reinforcing ring 104 abuts the valve sewing ring 42. Both the posts 92 and the ring 104 further include a series of through holes 106 that may be used to secure the polyester skirt 88 to the stent 36 using sutures or the like. A number of variants of the coupling stent 36 are also described below.

Figure 12A:
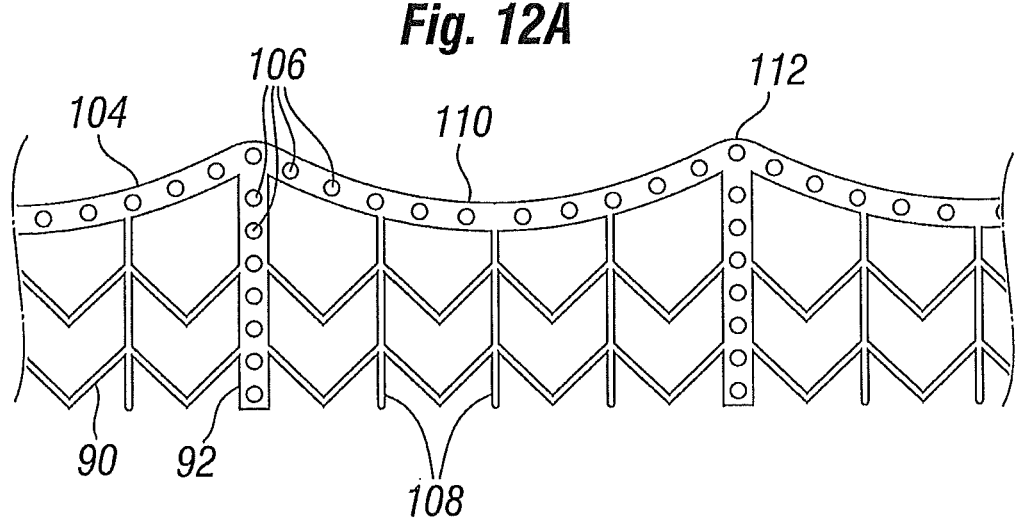
FIGS. 12A-12B illustrate an exemplary coupling stent in both a flat configuration (12A) and a tubular expanded configuration (12B)
Figure 12B:
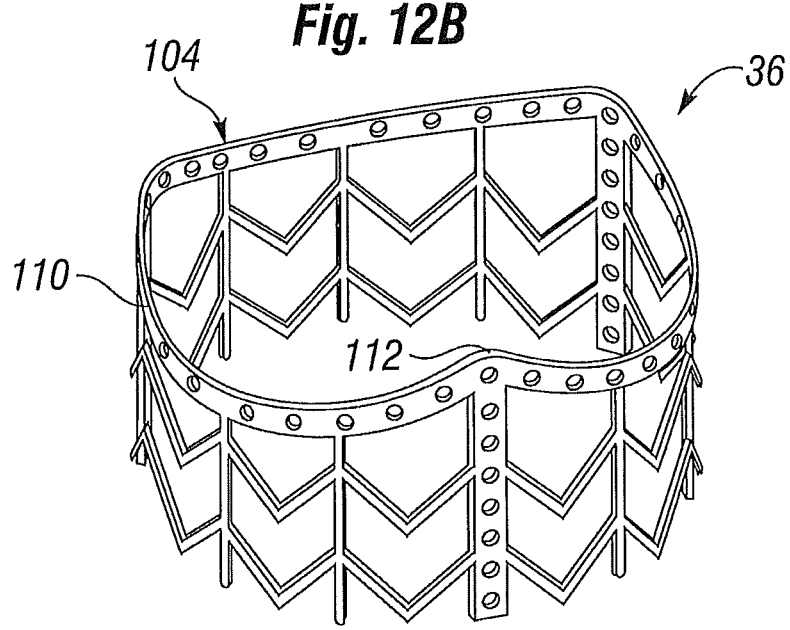

FIGS. 12A-12B illustrate the exemplary coupling stent 36 in both a flat configuration (12A) and a tubular configuration (12B) that is generally the expanded shape. As mentioned, the web-like struts 90 and a reinforcing ring 104 connect three generally axially-extending posts 92. A plurality of evenly spaced apertures 106 provide anchors for holding the polyester skirt 88 (see FIG. 11B) in place. In the illustrated embodiment, the web-like struts 90 also include a series of axially-extending struts 108. An upper end of the coupling stent 36 that connects to the sewing ring of the valve and is defined by the reinforcing ring 104 follows an undulating path with alternating arcuate troughs 110 and peaks 112. As seen from FIG. 11C, the exemplary prosthetic valve 34 has an undulating sewing ring 42 to which the upper end of the coupling stent 36 conforms. In a preferred embodiment, the geometry of the stent 36 matches that of the undulating sewing ring 42. Of course, if the sewing ring of the prosthetic valve is planar, then the upper end of the coupling stent 36 will also be planar. It should be noted also that the tubular version of FIG. 12B is an illustration of an expanded configuration, although the balloon 40 may over-expand the free (lower) end of the stent 36 such that it ends up being slightly conical.

Figure 13A:
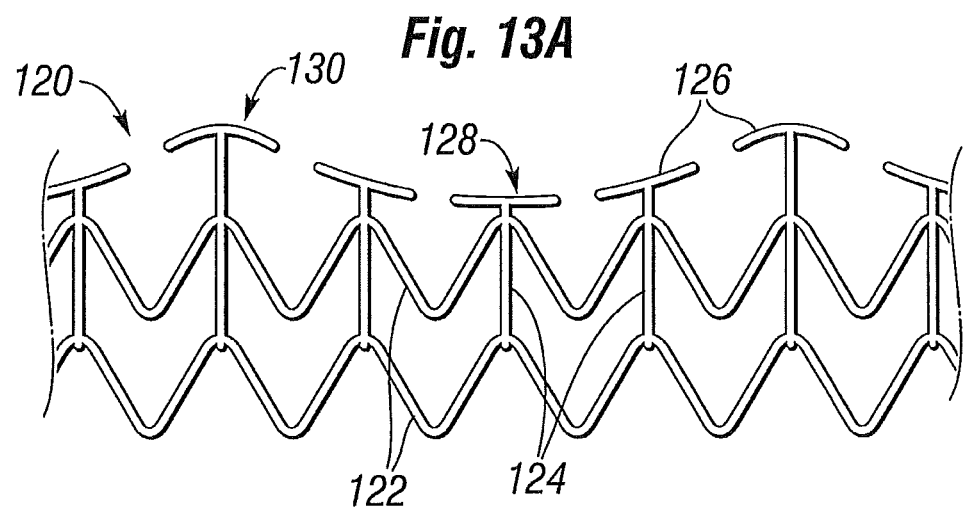
FIGS. 13A-13B illustrate an alternative coupling stent having a discontinuous upper end in both flat and tubular expanded configurations.
Figure 13B:
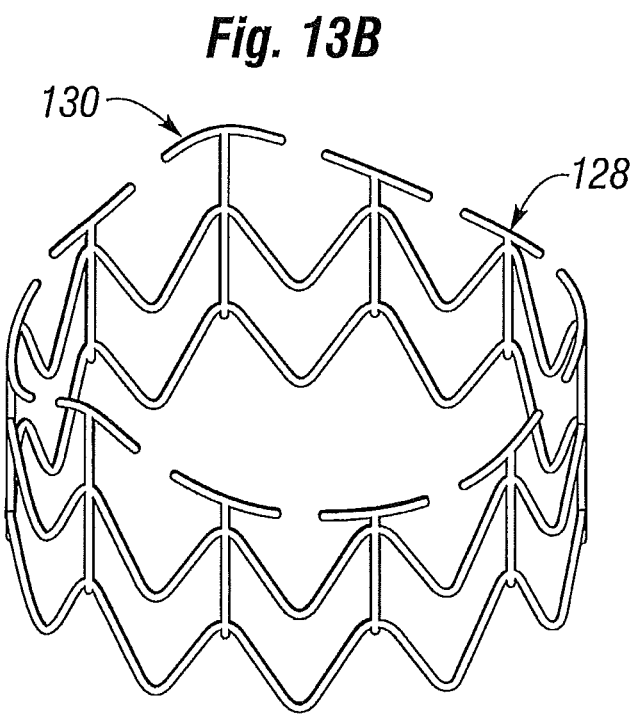

FIGS. 13A and 13B show an alternative coupling stent 120, again in flattened and tubular configurations, respectively. As with the first embodiment, the coupling stent 120 includes web-like struts 122 extending between a series of axially-extending struts 124. In this embodiment, all of the axially-extending struts 124 are substantially the same thin cross-sectional size. The upper or connected end of the stent 120 again includes a reinforcing ring 126, although this version is interrupted with a series of short lengths separated by gaps. The upper end defines a plurality of alternating troughs 128 and peaks 130, with lengths of the reinforcing ring 126 defining the peaks. The axially-extending struts 124 are in-phase with the scalloped shape of the upper end of the stent 120, and coincide with the peaks and the middle of the troughs.

The gaps between the lengths making up the reinforcing ring 126 permit the stent 120 to be matched with a number of different sized prosthetic valves 34. That is, the majority of the stent 120 is expandable having a variable diameter, and providing gaps in the reinforcing ring 126 allows the upper end to also have a variable diameter so that it can be shaped to match the size of the corresponding sewing ring. This reduces manufacturing costs as correspondingly sized stents need not be used for each different sized valve.

FIG. 14 is a plan view of a still further alternative coupling stent 132 that is very similar to the coupling stent 120, including web-like struts 134 connected between a series of axially-extending struts 136, and the upper end is defined by a reinforcing ring 138 formed by a series of short lengths of struts. In contrast to the embodiment of FIGS. 13A and 13B, the peaks of the undulating upper end have gaps as opposed to struts. Another way to express this is that the axially-extending struts 136 are out-of-phase with the scalloped shape of the upper end of the stent 132, and do not correspond to the peaks and the middle of the troughs.

FIG. 15 illustrates an exemplary coupling stent 140 again having the expandable struts 142 between the axially-extending struts 144, and an upper reinforcing ring 146. The axially-extending struts 144 are in-phase with peaks and troughs of the upper end of the stent. The reinforcing ring 146 is a cross between the earlier-described such rings as it is continuous around its periphery but also has a variable diameter. That is, the ring 146 comprises a series of lengths of struts 148 of fixed length connected by thinner bridge portions 150 of variable length. The bridge portions 150 are each formed with a radius so that they can be either straightened (lengthened) or bent more (compressed). A series of apertures 152 are also formed in an upper end of the stent 142 provide anchor points for sutures or other attachment means when securing the stent to the sewing ring of the corresponding prosthetic valve.

In FIG. 16, an alternative coupling stent 154 is identical to the stent 140 of FIG. 15, although the axially-extending struts 156 are out-of-phase with the peaks and troughs of the undulating upper end.

FIG. 17 shows a still further variation on a coupling stent 160, which has a series of expandable struts 162 connecting axially-extending struts 164. As with the version shown in FIGS. 12A and 12B, the web-like struts 162 also include a series of axially-extending struts 166, although these are thinner than the main axial struts 164. A reinforcing ring 168 is also thicker than the web-like struts 162, and features one or more gaps 170 in each trough such that the ring is discontinuous and expandable. Barbs 172, 174 on the axially extending struts 164, 166 may be utilized to enhance retention between the coupling stent 160 and a base stent with which it cooperates, or with annular tissue in situations where there is no base stent, as explained above.

As mentioned above, the two-component valve systems described herein utilize an outer or base stent (such as base stent 24) and a valve component having an inner or valve stent (such as coupling stent 36). The valve and its stent advance into the lumen of the pre-anchored outer stent and the valve stent expands to join the two stents and anchor the valve into its implant position. It is important that the inner stent and outer stent be correctly positioned both circumferentially and axially to minimize subsequent relative motion between the stents. Indeed, for the primary application of an aortic valve replacement, the circumferential position of the commissures of the valve relative to the native commissures is very important. A number of variations of coupling stent that attach to the valve component have been shown and described above. FIGS. 18-20 illustrate exemplary base stents and cooperation between the two stents.

FIGS. 18A and 18B show an exemplary embodiment of a base stent 180 comprising a plurality of radially-expandable struts 182 extending between a plurality of generally axially-extending struts 184. In the illustrated embodiment the struts 182 form chevron patterns between the struts 184, although other configurations such as serpentine or diamond-shaped could also be used. The top and bottom rows of the radially-expandable struts 182 are arranged in apposition so as to form a plurality of triangular peaks 186 and troughs 188. The axial struts 184 are in-phase with the troughs 188.

The flattened view of FIG. 18A shows four axial projections 190 that each extend upward from one of the axial struts 184. Although four projections 190 are shown, the exemplary base stent 180 desirably has three evenly circumferentially spaced projections, as seen around the periphery in the tubular version of FIG. 18B, providing location markers for the base stent. These markers thus make it easier for the surgeon to orient the stent 180 such that the markers align with the native commissures. Furthermore, as the valve component advances to within the base stent 180, the visible projections 190 provide reference marks such that the inner stent can be properly oriented within the base stent. In this regard the projections 190 may be differently colored than the rest of the stent 180, or have radiopaque indicators thereon.

The length of the projections 190 above the upper row of middle struts 182 may also be calibrated to help the surgeon axially position the stent 180. For example, the distance from the tips of the projections 190 to the level of the native annulus could be determined, and the projections 190 located at a particular anatomical landmark such as just below the level of the coronary ostia.

An undulating dashed line 192 in FIG. 18A represents the upper end of the inner or coupling stent 140, which is shown in phantom superimposed over the base stent 180. As such, the dashed line 192 also represents an undulating sewing ring, and it bears repeating that the sewing ring could be planar such that the upper end of the coupling stent is also planar. The coupling stent 140 includes axially-extending struts that are in-phase with the respective peaks and troughs of the scalloped upper end of the stent. In the illustrated combination, the peaks of the scalloped upper end of the coupling stent (dashed line 192) correspond rotationally (are in-phase) with the axial struts 184 that have the projections 190. Therefore, because the coupling stent 140 axial struts are in-phase with the peaks of the upper end thereof, they are also in-phase with the axial struts 184 of the base stent 180. Conversely, a coupling stent may have axial struts out-of-phase with peaks of the upper end thereof, in which case the respective axial struts of the two stents are also out-of-phase.

FIG. 19 shows an alternative base stent 200 that generally has the same components as the base stent 180 of FIG. 18A, but the axial struts 184 extend between the peaks 186 of the outer rows of middle struts 182. In the earlier embodiment, the axial struts 184 extended between the troughs 188. The coupling stent 154 of FIG. 16 is shown in phantom superimposed over the base stent 200 to illustrate how the axial struts of the two stents are now out-of-phase to increase interlocking therebetween.

The stent 200 also exhibits different rows of middle struts 182. Specifically, a first row 202a defines V's having relatively shallow angles, a second row 202b defines V's with medium angles, and a third row 202c defined V's with more acute angles. The different angles formed by the middle struts 182 in these rows helps shape the stent into a conical form when expanded. There is, the struts in the third row 202c which is farthest from the prosthetic valve have the greatest capacity for expansion to accommodate the transition from the collapsed conical shape of the stent to the expanded tubular shape.

Those of skill in the art will understand that there are many ways to increase retention between the two stents. For example, the peaks and troughs of the web-like expandable struts on the two stents could be oriented out-of-phase or in-phase. In a preferred embodiment the peaks and troughs of the two stents are out of phase so that expansion of the inner stent causes its peaks to deform outwardly into the troughs of the outer stent, and thereby provide interlocking structure therebetween. The variations described above provide a number of permutations of this cooperation.

Additionally, axial projections on one or both of stents could be bent to provide an interference with the other stent. For example, the lower ends of the axial struts 108 in the stent 36 shown in FIG. 12A could be bent outward by expansion of a non-uniform shaped balloon such that they extend in voids within the outer stent. Likewise, the embodiment of FIG. 17 illustrates barbs 172, 174 that can be bent outward into interference with the corresponding base stent. Strut ends or barbs that transition from one position to another to increase retention between the two stents can be actuated by mechanical bending, such as with a balloon, or through an automatic shape change upon installation within the body. Namely, some shape memory alloys such as Nitinol can be designed to undergo a shape change upon a temperature change, such that they assume a first shape at room temperature, and a second shape at body temperature.

FIG. 20 illustrates a simplified means for increasing retention between the two stents. An inner valve stent 210 fits within an outer base stent 212 such that a lower end 214 thereof extends below the outer stent. By over-expansion of the balloon within the inner stent 210, the lower end 214 is caused to bend or wrap outward to prevent relative upward movement of the inner stent within the outer stent.

Figure 21:
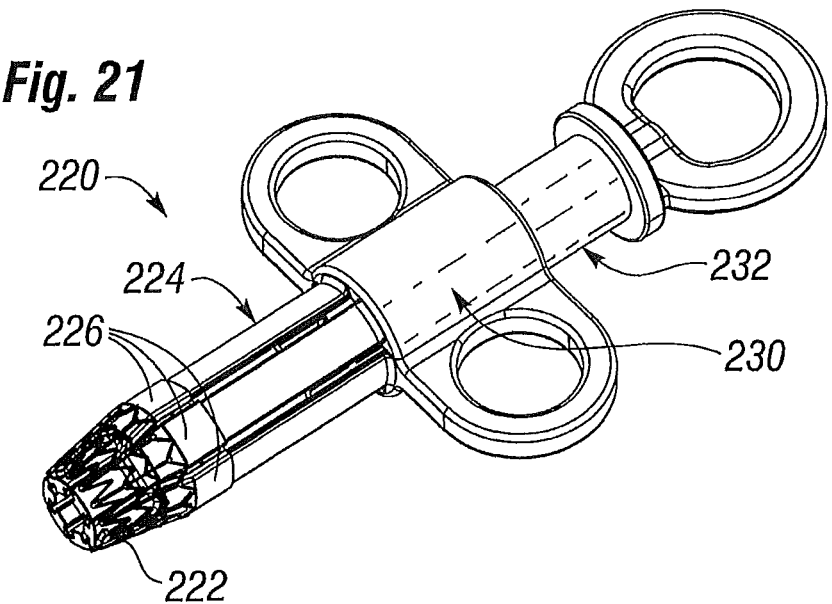
FIG. 21-23 is a perspective view of a device for delivering and expanding a base stent with mechanical fingers.
Figure 22:
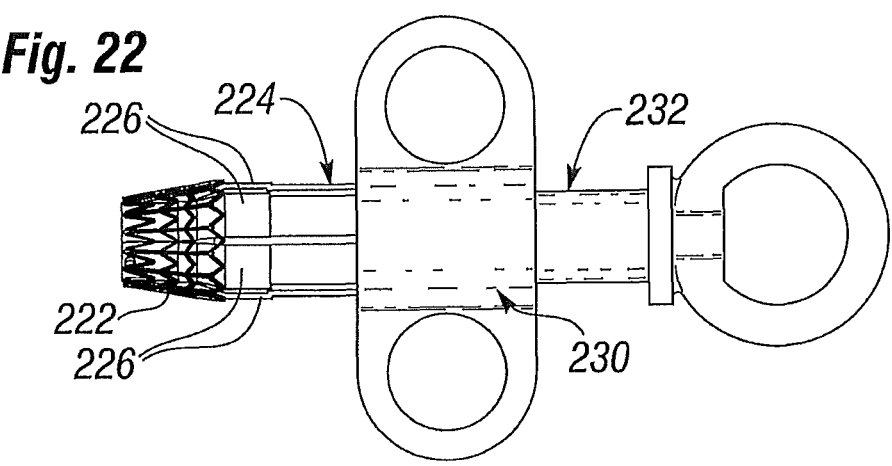
Figure 23:
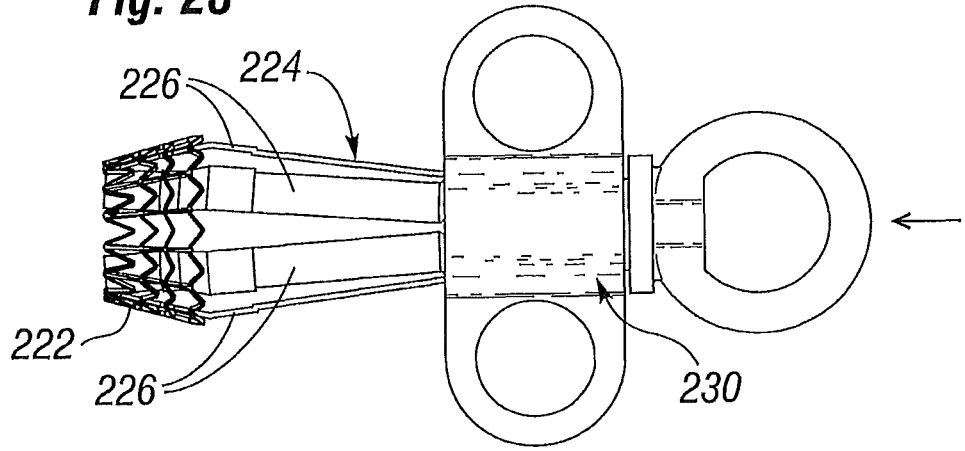

FIG. 21 is a perspective view of a device 220 for delivering and expanding a base stent 222 with a mechanical expander 224. In the illustrated embodiment, the expander 224 includes a plurality of spreadable fingers 226 over which the base stent 22 is crimped. The device 220 includes a syringe-like apparatus including a barrel 230 within which a plunger 232 linearly slides. The fingers 226 are axially fixed but capable of pivoting or flexing with respect to the barrel 230. The distal end of the plunger 232 has an outer diameter that is greater than the diameter circumscribed by the inner surfaces of the spreadable fingers 226. Preferably there is a proximal lead-in ramp on the inside of the fingers 226 such that distal movement of the plunger 232 with respect to the barrel 230 gradually cams the fingers outward. The two positions of the plunger 232 are shown in FIGS. 21 and 23.

As an alternative to simple linear movement of the plunger 232, it may also be threadingly received within the barrel 230. Still further, the plunger 232 may be formed in two parts freely rotatable with respect to one another, with a proximal part threadingly received within the barrel 230 while a distal part does not rotate with respect to the barrel and merely cams the fingers 226 outward. Still further, a mechanical linkage may be used instead of a camming action whereby levers hinged together create outward movement of the fingers 226. And even further still, a hybrid version using an inflatable balloon with mechanical parts mounted on the outside of the balloon may be utilized. Those of skill in the art will understand that numerous variants on this mechanism are possible, the point being that balloon expansion is not only vehicle.

Desirably, the fingers 226 have a contoured exterior profile such that they expand the base stent 222 into a particular shape that better fits the heart valve annulus. For instance, the base stent 222 may be expanded into an hourglass shape with wider upper and lower ends and a smaller midsection, and/or an upper end may be formed with a tri-lobular shape to better fit the aortic sinuses. In the latter case, the tri-lobular shape is useful for orienting the base stent 222 upon implant, and also for orienting the coupling stent of the valve component that is received therewithin.

In another advantageous feature, the two-component valve system illustrated in the preceding figures provides a device and method that substantially reduces the time of the surgical procedure as compared with replacement valves that are sutured to the tissue after removing the native leaflets. For example, the stent 24 of FIGS. 5-9 may be deployed quickly and the valve component 30 may also be quickly attached to the stent. This reduces the time required on extracorporeal circulation and thereby substantially reduces the risk to the patient.

In addition to speeding up the implant process, the present invention having the pre-anchored stent, within which the valve and its stent mount, permits the annulus to be expanded to accommodate a larger valve than otherwise would be possible. In particular, clinical research has shown that the left ventricular outflow tract (LVOT) can be significantly expanded by a balloon-expandable stent and still retain normal functioning. In this context, "significantly expanding" the LVOT means expanding it by at least 10%, more preferably between about 10-30%. In absolute terms, the LVOT may be expanded 1.5-5 mm depending on the nominal orifice size. This expansion of the annulus creates an opportunity to increase the size of a surgically implanted prosthetic valve. The present invention employs a balloon-expandable base stent, and a balloon-expandable valve stent. The combination of these two stents permits expansion of the LVOT at and just below the aortic annulus, at the inflow end of the prosthetic valve. The interference fit created between the outside of the base stent and the LVOT secures the valve without pledgets or sutures taking up space, thereby allowing for placement of the maximum possible valve size. A larger valve size than would otherwise be available with conventional surgery enhances volumetric blood flow and reduces the pressure gradient through the valve.

It will be appreciated by those skilled in the art that embodiments of the present invention provide important new devices and methods wherein a valve may be securely anchored to a body lumen in a quick and efficient manner. Embodiments of the present invention provide a means for implanting a prosthetic valve in a surgical procedure without requiring the surgeon to suture the valve to the tissue. Accordingly, the surgical procedure time is substantially decreased. Furthermore, in addition to providing a base stent for the valve, the stent may be used to maintain the native valve in a dilated condition. As a result, it is not necessary for the surgeon to remove the native leaflets, thereby further reducing the procedure time.

It will also be appreciated that the present invention provides an improved system wherein a valve member may be replaced in a more quick and efficient manner. More particularly, it is not necessary to cut any sutures in order to remove the valve. Rather, the valve member may be disconnected from the stent (or other base stent) and a new valve member may be connected in its place. This is an important advantage when using biological tissue valves or other valves having limited design lives.

While the invention has been described in its preferred embodiments, it is to be understood that the words which have been used are words of description and not of limitation. Therefore, changes may be made within the appended claims without departing from the true scope of the invention.

What is claimed is:

1. A system for delivering a prosthetic heart valve, comprising:
   a valve component including a non-expandable, non-collapsible prosthetic valve surrounding a flow orifice, the valve component further including an expandable coupling stent extending from an inflow end or distal end of the prosthetic valve, the coupling stent having a contracted state for delivery to an implant position and an expanded state;
   a valve holder connected to the prosthetic valve of the valve component opposite the coupling stent;
   a balloon catheter having a balloon; and
   a handle configured to attach to a proximal end of the valve holder and having a lumen for passage of the catheter, the balloon extending distally through the handle lumen, past the holder and through the valve component.

2. The system of claim 1, wherein the prosthetic valve comprises a bioprosthetic valve having flexible bioprosthetic leaflets, and wherein the coupling stent is fabric covered.

3. The system of claim 1, wherein the contracted state of the coupling stent is conical, tapering down in a distal direction.

4. The system of claim 1, wherein the contracted state of the coupling stent is conical and tapers down in a distal direction, and wherein the balloon catheter further includes a generally conical nose cone on a distal end thereof that extends through the valve component and engages a distal end of the coupling stent in its contracted state.

5. The system of claim 1, wherein the handle comprises a proximal section and a distal section that may be coupled together in series to form a continuous lumen, and wherein the distal section is adapted to couple to the hub of the valve holder to enable manual manipulation of the valve component using the distal section prior to connection with the proximal section.

6. The system of claim 5, wherein the balloon catheter and proximal handle section are packaged together with the balloon within the proximal section lumen.

7. The system of claim 1, wherein the valve component mounted on the holder is packaged separately from the handle and the balloon catheter.

8. A system for delivering a prosthetic heart valve, comprising:
- a hybrid prosthetic heart valve including both a non-expandable, non-collapsible prosthetic valve and an expandable stent on a distal end, the non-expandable, non-collapsible prosthetic valve surrounding a flow orifice and the expandable stent having a contracted state for delivery to an implant position and an expanded state;
- a valve holder connected to the non-expandable, non-collapsible prosthetic valve of the heart valve, the valve holder defining a throughbore;
- a handle configured to attach to a proximal end of the valve holder and having a lumen; and
- a balloon catheter having a balloon, wherein the balloon catheter slides within the handle lumen and includes a proximal coupling member that is spaced from a proximal end of the handle when the balloon is within the handle lumen and contacts the proximal end of the handle when the balloon is advanced to be located within the expandable stent for expansion thereof.

9. The system of claim 8, wherein the prosthetic valve comprises a bioprosthetic valve having flexible bioprosthetic leaflets, and wherein the expandable stent is a fabric covered coupling stent.

10. The system of claim 8, wherein the contracted state of the expandable stent is conical, tapering down in a distal direction.

11. The system of claim 8, wherein the expanded state of the expandable stent is conical, tapering outward in a distal direction, and the balloon has a larger distal expanded end than a proximal expanded end so as to expand the expandable stent conically outward.

12. The system of claim 8, further including a generally conical nose cone on a distal end of the balloon that extends through the heart valve and engages a distal end of the expandable stent in its contracted state.

13. The system of claim 8, wherein the handle comprises a proximal section and a distal section that may be coupled together in series to form a continuous lumen, and wherein the distal section is adapted to couple to the hub of the valve holder to enable manual manipulation of the heart valve using the distal section prior to connection with the proximal section.

* * * * *